United States Patent [19]

Condon et al.

[11] Patent Number: 5,545,742
[45] Date of Patent: Aug. 13, 1996

[54] 6-HETEROCYCLYL-1-(SUBSTITUTED PHENYL) BENZOTRIAZOLE HERBICIDAL AGENTS

[75] Inventors: Michael E. Condon, Mercer; Alvin D. Crews, Jr., Camden; Mark C. Manfredi, Mercer, all of N.J.

[73] Assignee: American Cyanamid Co., Madison, N.J.

[21] Appl. No.: 437,112

[22] Filed: May 5, 1995

Related U.S. Application Data

[63] Continuation of Ser. No. 387,140, Feb. 10, 1995.
[51] Int. Cl.$^6$ .................. C07D 249/18; C07D 405/12
[52] U.S. Cl. ..................... 548/261; 548/259; 548/260
[58] Field of Search ....................... 548/259, 260, 548/261

[56] References Cited

U.S. PATENT DOCUMENTS 4,755,215  7/1988  Haga et al. .................. 71/92

Primary Examiner—Patricia L. Morris
Attorney, Agent, or Firm—Joseph M. Mazzarese

[57] ABSTRACT

There is provided a 6-heterocyclyl-1-(substituted phenyl)benzotriazole compound having the structural formula I

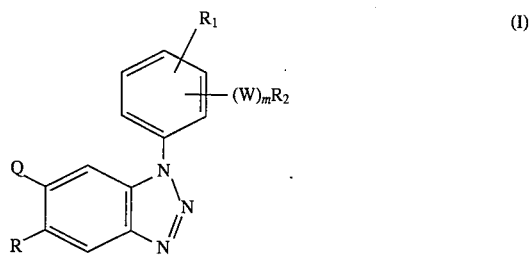

Further provided are a composition and a method comprising that compound for the control of undesirable plant species.

2 Claims, No Drawings

6-HETEROCYCLYL-1-(SUBSTITUTED PHENYL) BENZOTRIAZOLE HERBICIDAL AGENTS

This is a continuation of copending application Ser. No. 08/387,140 filed on Feb. 10, 1995.

BACKGROUND OF THE INVENTION

Weeds cause tremendous global economic losses by reducing crop yields and lowering crop quality. In the United States alone, agronomic crops must compete with hundreds of weed species.

In spite of the commercial herbicides available today, damage to crops caused by weeds still occurs. Accordingly, there is ongoing research to create new and more effective herbicides.

It is an object of the present invention to provide compounds which are highly effective for controlling undesirable plant species.

It is also an object of the present invention to provide methods for controlling undesirable plant species.

These and other objects of the present invention will become more apparent from the detailed description thereof set forth below.

SUMMARY OF THE INVENTION

The present invention describes 6-heterocyclyl-1-(substituted phenyl)benzotriazole compounds which are useful as herbicidal agents.

The 6-heterocyclyl-1-(substituted phenyl)benzotriazole compounds of the present invention have the structural formula I

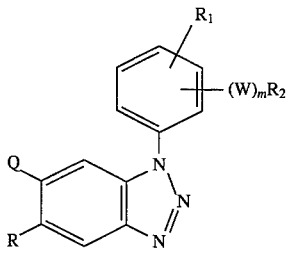

wherein
R is hydrogen, halogen, nitro, cyano, $C_1$–$C_4$alkyl, $C_1$–$C_4$haloalkyl, $C_1$–$C_4$alkoxy, $C_1$–$C_4$haloalkoxy or $R_3S(O)n$;

$R_3$ is $C_1$–$C_4$alkyl optionally substituted with one or more halogen atoms;

n is an integer of 0, 1 or 2;

$R_1$ is hydrogen, halogen, $C_1$–$C_4$alkyl or $C_1$–$C_4$haloalkyl;

$R_2$ is V or $R_4V$;

$R_4$ is $C_1$–$C_5$alkylene optionally substituted with one or more halogen, $C_1$–$C_4$alkyl, $C_1$–$C_4$haloalkyl or $C_3$–$C_6$cycloalkyl groups;

V is hydrogen, halogen, cyano, $C(O)R_5$, $C(Y)R_6$, $CH_2OC(O)R_7$, $CH_2OR_6$, $CH(OR_8)_2$, $N(R_6)SO_2R_9$, $C_2$–$C_6$alkenyl substituted with one $CO_2R_7$ group or $C_2$–$C_6$alkynyl substituted with one $CO_2R_7$ group;

$R_5$ is OH, $OR_{10}$, $NR_{11}R_{12}$ or $N(R_6)SO_2R_9$;

Y is O, $NOC(R_{13}R_{14})CO_2R_8$ or $NOR_7$;

$R_6$ is hydrogen or $C_1$–$C_4$alkyl optionally substituted with $C_1$–$C_4$alkoxy;

$R_7$ is hydrogen, $C_1$–$C_4$alkyl, benzyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups;

$R_8$ is $C_1$–$C_4$alkyl, —$(CH_2)_3$— or —$(CH_2)_4$—;

$R_9$ is $C_1$–$C_4$alkyl, $C_1$–$C_4$haloalkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups;

$R_{10}$ is $C_1$–$C_6$alkyl optionally substituted with $C_1$–$C_4$alkoxy, $C_1$–$C_4$alkylthio, halogen, hydroxy, $C_3$–$C_6$cycloalkyl, furyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$ haloalkoxy groups, $C_3$–$C_6$alkenyl optionally substituted with $C_1$–$C_4$alkoxy, halogen, $C_3$–$C_6$cycloalkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups, $C_3$–$C_6$alkynyl optionally substituted with $C_1$–$C_4$alkoxy or halogen, $C_3$–$C_6$cycloalkyl, $N=C(R_{13}R_{14})$, $C(R_{13}R_{14})CO_2R_6$ or an alkali metal, alkaline earth metal, manganese, copper, zinc, cobalt, silver, nickel, ammonium or organic ammonium cation;

$R_{11}$ and $R_{12}$ are each independently hydrogen, $C_1$–$C_4$alkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups;

$R_{13}$ and $R_{14}$ are each independently hydrogen or $C_1$–$C_4$alkyl;

W is O, S or $NR_{15}$;

$R_{15}$ is hydrogen or $C_1$–$C_4$alkyl;

m is an integer of 0 or 1;

Q is selected from

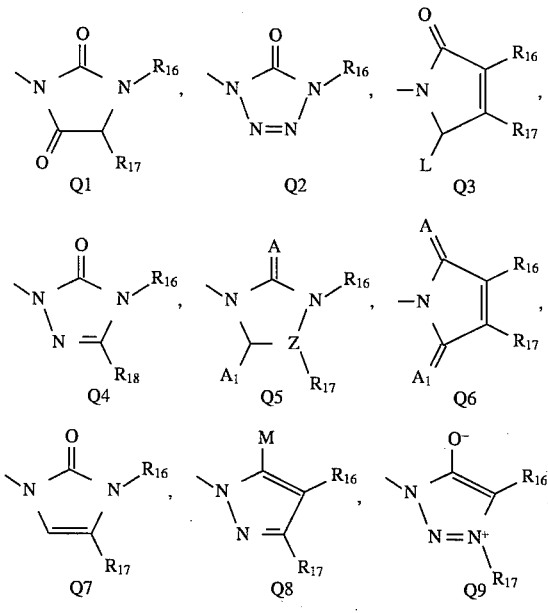

3
-continued

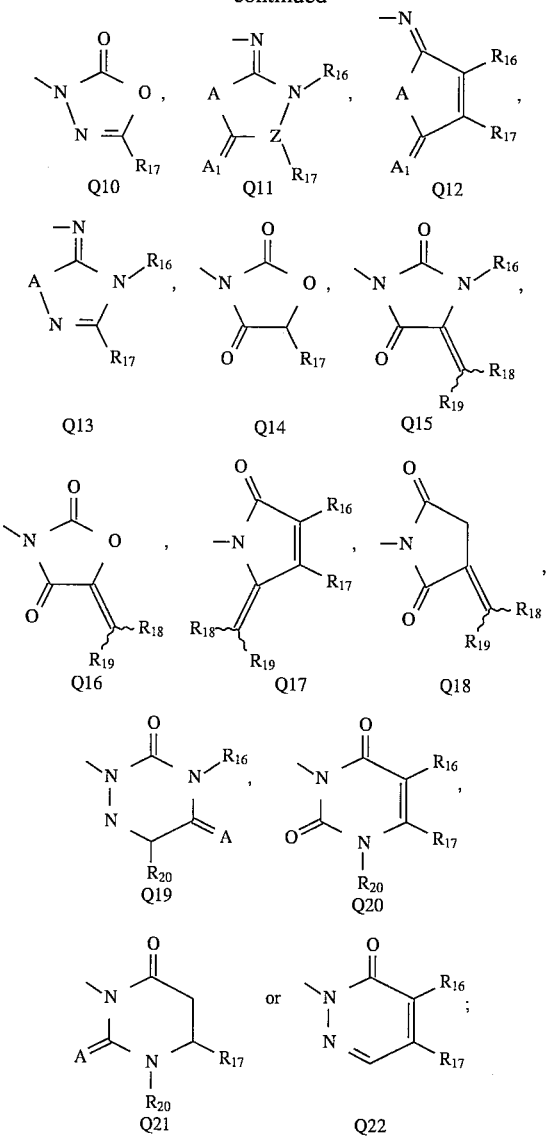

$R_{16}$ and $R_{17}$ are each independently hydrogen,
  $C_1$–$C_6$alkyl optionally substituted with one or more halogen atoms, or
  $C_3$–$C_6$cycloalkyl optionally substituted with one or more halogen atoms, and
  when $R_{16}$ and $R_{17}$ are taken together with the atoms to which they are attached, they represent a four- to seven-membered saturated or unsaturated ring optionally interrupted by O, S or N, and optionally substituted with one to three methyl groups or one or more halogen atoms.

$R_{18}$, $R_{19}$ and $R_{20}$ are each independently hydrogen or $C_1$–$C_3$alkyl;

A and $A_1$ are each independently O or S;

L is hydroxy, halogen, $C_1$–$C_3$alkoxy or $C_1$–$C_3$alkylthio;

M is halogen or $C_1$–$C_3$alkyl; and

Z is N or CH.

This invention also relates to compositions containing those compounds and methods for using those compounds and compositions. Advantageously, it has been found that the compounds of the present invention, and compositions containing them, are useful for the control of undesirable plant species. The compounds of the present invention are especially useful for the control of undesirable plant species in the presence of crop plants.

DETAILED DESCRIPTION OF THE INVENTION

The present invention provides a method for controlling undesirable plant species which comprises applying to the foliage of said plants or to the soil or water containing seeds or other propagating organs thereof, a herbicidally effective amount of a formula I, 6-heterocyclyl-1-(substituted phenyl)benzotriazole compound.

The 6-heterocyclyl-1-(substituted phenyl)benzotriazole compounds of the present invention have the structural formula I

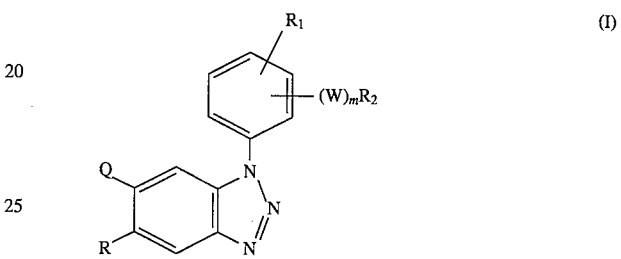

wherein R, $R_1$, $R_2$, W, m and Q are as described above.

Preferred formula I 6-heterocyclyl-1-(substituted phenyl)benzotriazole compounds of this invention are those wherein R is hydrogen or halogen;

$R_1$ is hydrogen or $C_1$–$C_4$alkyl;

$R_2$ is V or $R_4$V;

$R_4$ is methylene optionally substituted with one or two halogen atoms, one $C_1$–$C_4$alkyl group or one $C_1$–$C_4$haloalkyl group;

V is hydrogen, halogen, C(O)$R_5$ or $C_2$–$C_6$alkynyl;

$R_5$ is OH or OR$_{10}$;

$R_{10}$ is $C_1$–$C_6$alkyl;

W is O;

m is an integer of 0 or 1;

Q is

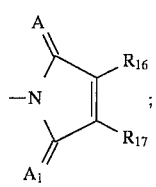

$R_{16}$ and $R_{17}$ are each independently hydrogen,
  $C_1$–$C_6$alkyl optionally substituted with one or more halogen atoms, or
  $C_3$–$C_6$cycloalkyl optionally substituted with one or more halogen atoms, and
  when $R_{16}$ and $R_{17}$ are taken together with the atoms to which they are attached, they may form a ring in which $R_{16}R_{17}$ is a $C_2$–$C_5$alkylene group optionally substituted with one to three methyl groups or one or more halogen atoms; and A and $A_1$ are each independently O or S.

More preferred formula I herbicidal agents of the present invention are those wherein R is hydrogen or F;

$R_1$ is hydrogen or methyl;
$R_2$ is V or $R_4V$;
$R_4$ is methylene optionally substituted with two fluorine atoms or one methyl group;
V is hydrogen, F, $CO_2H$ or $CO_2CH_3$;
W is O;
n is an integer of 0 or 1;
Q is

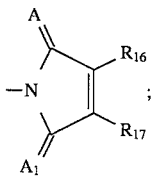   Q6

$R_{16}$ and $R_{17}$ are taken together with the atoms to which they are attached to form a ring in which $R_{16}R_{17}$ is a butylene group optionally substituted with one to three methyl groups or one or more halogen atoms; and
A and $A_1$ are O.

Most preferred formula I compounds of this invention which are especially useful for the control of undesirable plant species are those wherein R is F;
$R_1$ is hydrogen;
$R_2$ is methyl, trifluoromethyl or $R_4V$;
$R_4$ is methylene optionally substituted with one methyl group;
V is $CO_2H$ or $CO_2CH_3$;
W is O;
m is an integer of 0 or 1; and
Q is

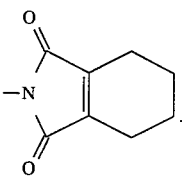

6-Heterocyclyl-1-(substituted phenyl)benzotriazole compounds of the present invention which are particularly effective herbicidal agents include
methyl {o-[6-(1-cyclohexene-1,2-dicarboximido)-5-fluoro-1H-benzotriazol-1-yl]phenoxy}acetate;
methyl 2-{o-[6-(1-cyclohexene-1,2-dicarboximido)-5-fluoro-1H-benzotriazol-1-yl]phenoxy}propionate;
N-[5-fluoro-1-(p-tolyl)-1H-benzotriazol-6-yl]-1-cyclohexene- 1,2-dicarboximide;
N-[5-fluoro-1-(o-methoxyphenyl)-1H-benzotriazol-6-yl]-1 -cyclohexene-1,2-dicarboximide;
{o-[6-(1-cyclohexene-1,2-dicarboximido)-5-fluoro-1 H-benzotriazol-1-yl]phenoxy}acetic acid;
N-[5-fluoro-1-(p-methoxyphenyl)-1H-benzotriazol-6-yl]-1 -cyclohexene-1,2-dicarboximide;
methyl 2-{p-[6-(1-cyclohexene-1,2-dicarboximido)-5-fluoro-1H-benzotriazol-1-yl]phenoxy}propionate; and
N-{5-fluoro-1-[p-(trifluoromethoxy)phenyl]-1H-benzotriazol- 6-yl}-1-cyclohexene-1,2-dicarboximide, among others.

Exemplary of halogen hereinabove are flourine, chlorine, bromine and iodine. The terms $C_1$–$C_4$haloalkyl and $C_1$–$C_4$haloalkoxy as used in the specification and claims designates a $C_1$–$C_4$alkyl group or a $C_1$–$C_4$alkoxy group substituted with one or more halogen atoms, respectively. In formula I above, alkali metals include: sodium, potassium and lithium. Alkaline earth metals of formula I include magnesium and calcium. Further, the term organic ammonium is defined as a group consisting of a positively charged nitrogen atom joined to from one to four aliphatic groups, each containing from one to sixteen carbon atoms.

It has now been found that the compounds of the present invention are especially useful for the selective control of undesirable plant species in the presence of important agronomic crops.

6-Heterocyclyl-1-(substituted phenyl)benzotriazole compounds of the present invention wherein Q is Q1 may be prepared by converting a 6-amino-1-(substituted phenyl)benzotriazole of formula II to its corresponding isocyanate of formula III using standard methods such as phosgene in an inert solvent or palladium chloride and carbon monoxide. The formula III compound is then treated with an amino acid of formula IV, an amino ester of formula V in the presence of triethylamine followed by treatment of the intermediate urea of formula VI with ethanolic hydrogen chloride, or an α-bromocarboxamide of formula VII in the presence of a base such as potassium t-butoxide to form the desired compound. The above reaction schemes are shown below in Flow Diagram I.

FLOW DIAGRAM I

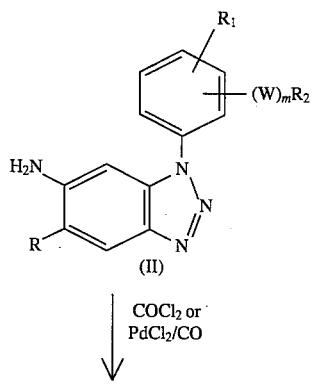

-continued
FLOW DIAGRAM I

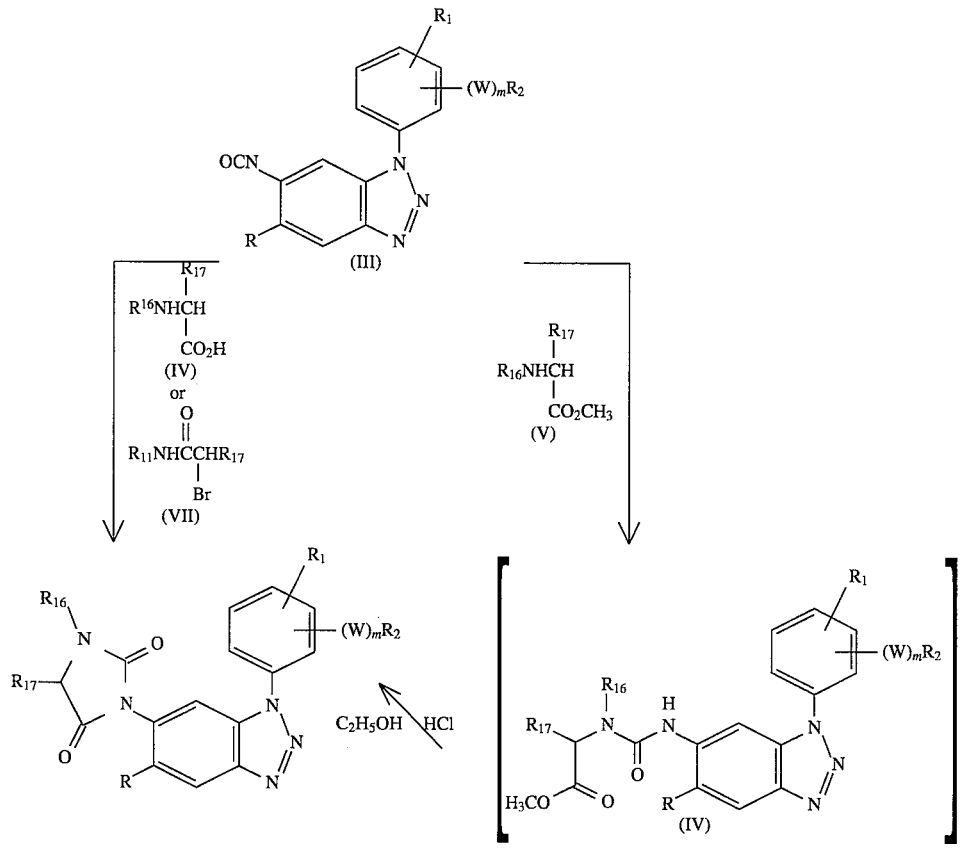

Compounds of formula I wherein Q is Q2 may be prepared by converting a 6-amino-1-(substituted phenyl-)benzotriazole of formula II to its corresponding azide of formula VIII by treatment with sodium nitrite, sodium azide, acetic acid, hydrogen chloride and sodium acetate or with sodium nitrite, hydrazine hydrate and acetic acid. The formula VIII compound is then treated with an isocyanate of formula IX to form the desired product. The above reaction scheme is shown in Flow Diagram II.

FLOW DIAGRAM II

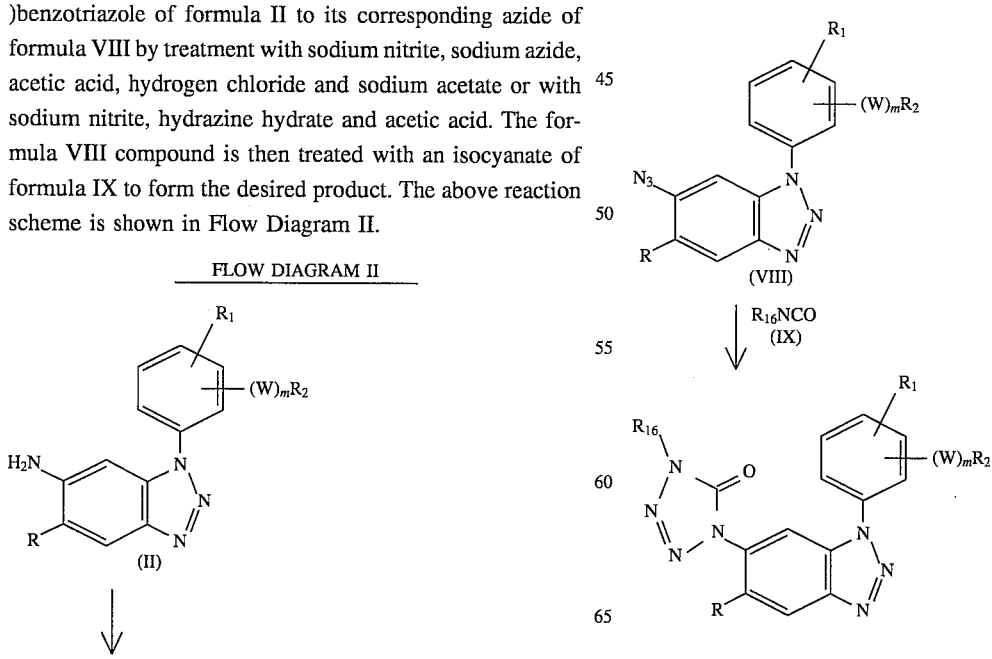

Alternatively, compounds of formula I wherein Q is Q2 may be prepared by reacting an isocyanate of formula III with trimethyl silylazide to form a compound of formula X and alkylating the formula X compound by conventional means. The reactions are shown below in Flow Diagram III.

FLOW DIAGRAM III

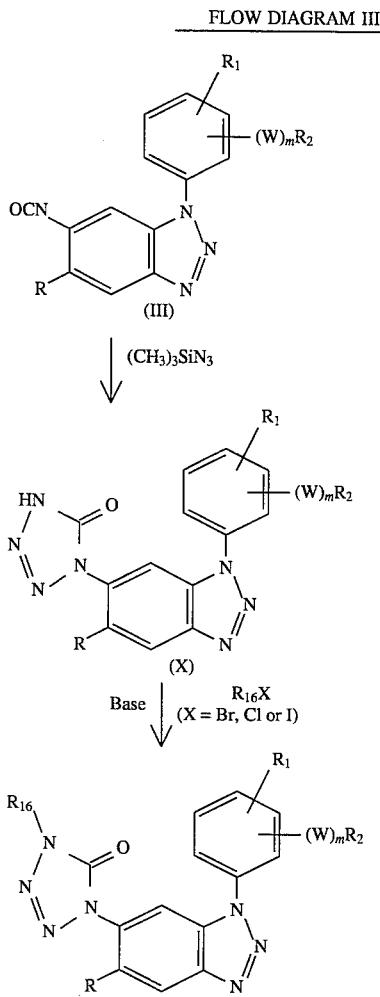

Formula I compounds wherein Q is Q6 and A and $A_1$ are oxygen may be prepared by reacting a 6-amino-1-(substituted phenyl)benzotriazole of formula II with an anhydride compound of formula XI, preferably at an elevated temperature. The reaction is shown in Flow Diagram IV.

FLOW DIAGRAM IV

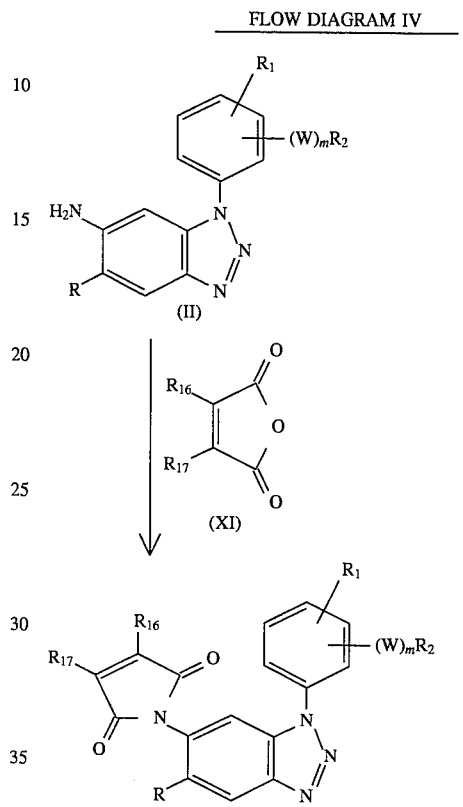

Formula I compounds wherein Q is Q6 and at least one of A or $A_1$ is sulfur may be prepared by treating a formula I compound wherein Q is Q6 and A and $A_1$ are oxygen with phosphorus pentasulfide or Lawesson's reagent (2,4-bis(4-methoxy-phenyl)-1,3-dithia-2,4-diphosphetane-2,4-disulfide) in an inert solvent such as toluene, xylene or chloroform.

Compounds of formula I wherein Q is Q3 may be prepared by reacting a compound of formula I wherein Q is Q6 and A and $A_1$ are oxygen with sodium borohydride to form a compound wherein L is OH, reacting the compound wherein L is OH with a base and a suitable alkylating agent to form a compound wherein L is $C_1$–$C_3$alkoxy or reacting the compound wherein L is OH with a halogenating agent such as phosphorus trichloride, thionyl chloride, phosphorus tribromide, triphenyl phosphine-bromine, phosphorus triiodide or triphenyl phosphine-iodine in an inert solvent such as chloroform to form a compound wherein L is halogen and further reacting the compound wherein L is halogen with a $C_1$–$C_3$alkyl sulfide to form a compound wherein L is $C_1$–$C_3$alkylthio. The above reaction schemes are shown in Flow Diagram V.

FLOW DIAGRAM V

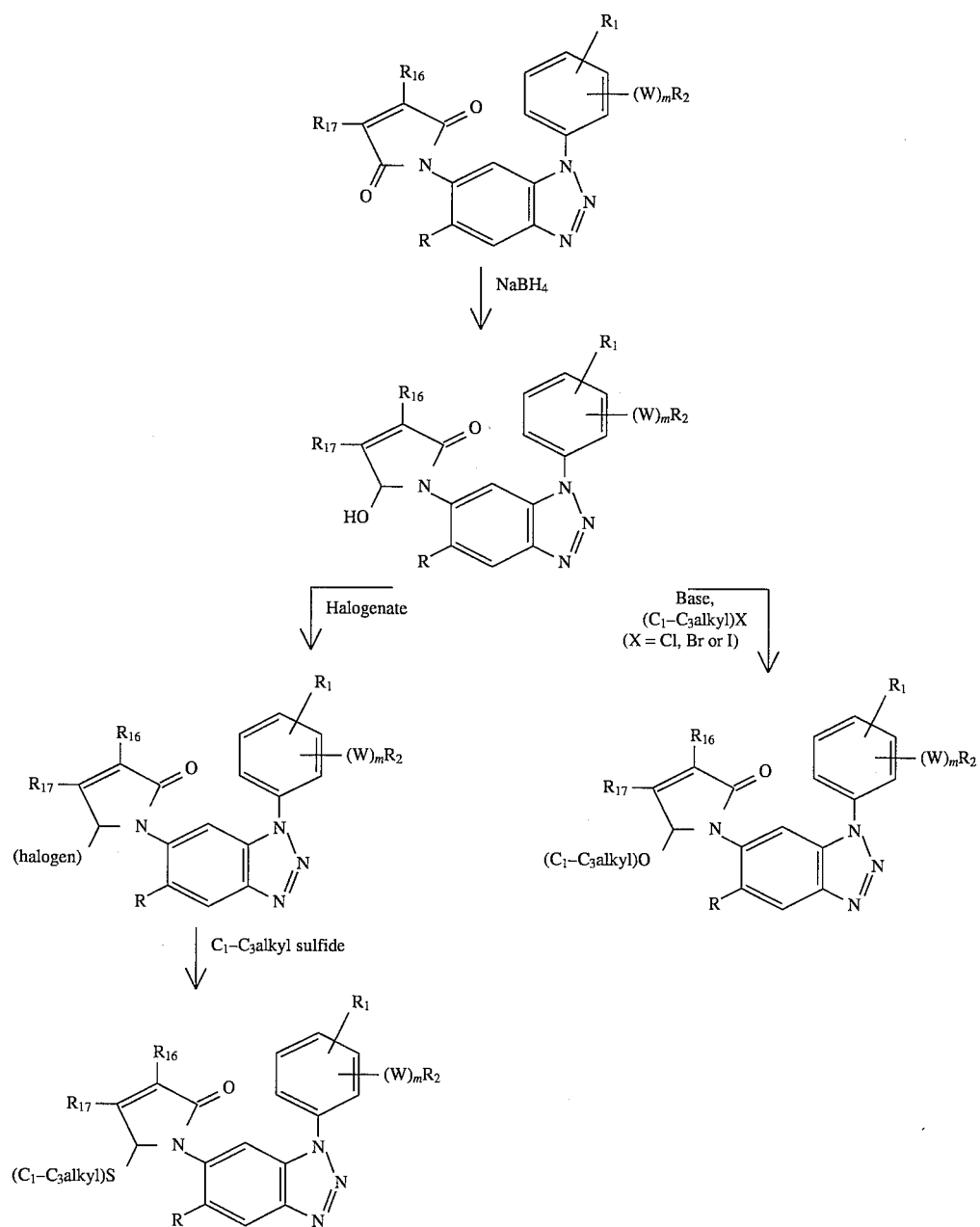

Formula I compounds wherein Q is Q5, Z is nitrogen and A and $A_1$ are oxygen may be prepared by reacting an isocyanate of formula III with a substituted N-alkoxycarbonyl hydrazine of formula XI to form an intermediate compound and reacting the intermediate compound with a base to obtain the desired compound. The reaction scheme is shown in Flow Diagram VI.

FLOW DIAGRAM VI

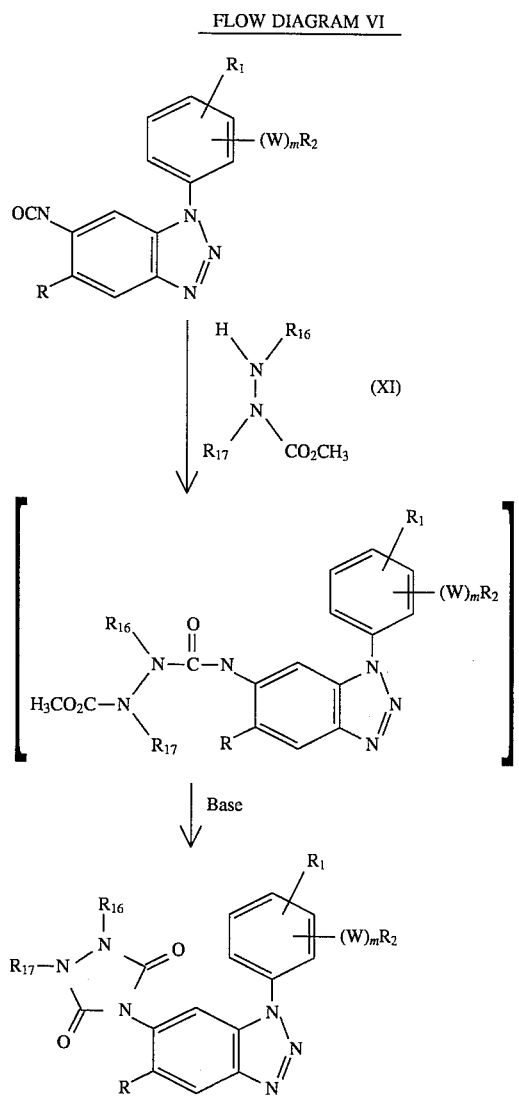

Similarly, formula I compounds wherein Q is Q5, Z is nitrogen, A is sulfur and $A_1$ is oxygen may be prepared by reacting a 6-amino-1-(substituted phenyl)benzotriazole of formula II with thiophosgene to form an isothiocyanate of formula XII, reacting the isothiocyanate with a substituted N-alkoxycarbonyl hydrazine of formula XI to form an intermediate compound and reacting the intermediate compound with a base. The reaction scheme is shown below in Flow Diagram VII.

FLOW DIAGRAM VII

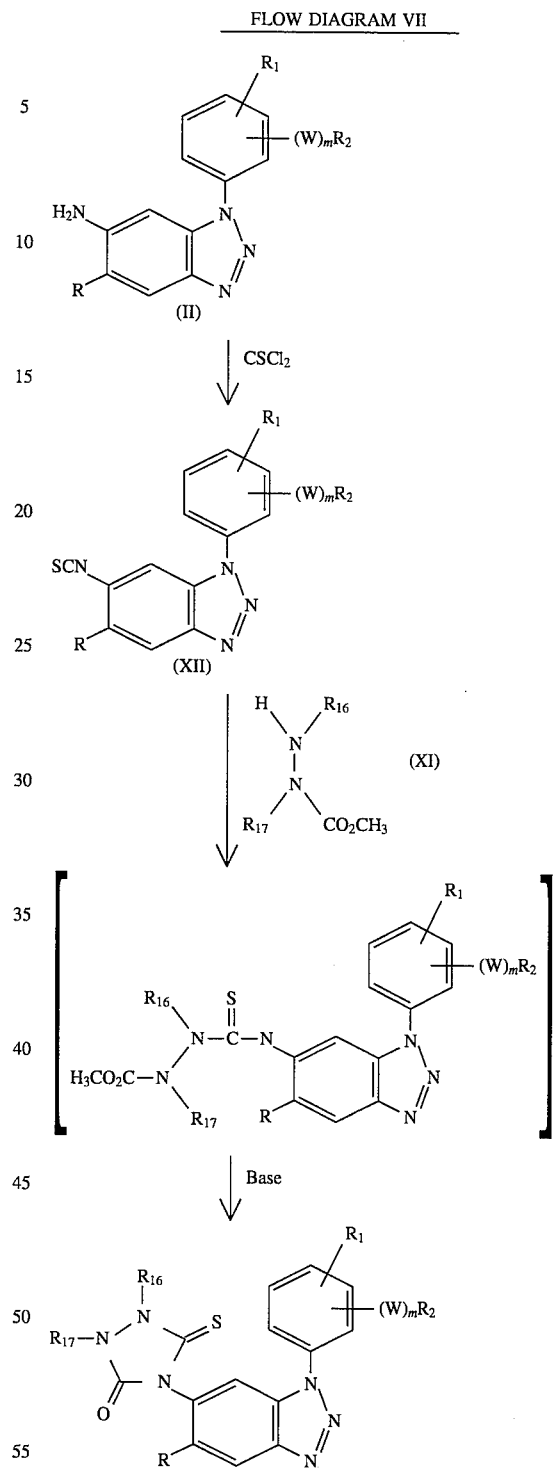

Compounds of formula I wherein Q is Q5, Z is CH, A is sulfur and $A_1$ is oxygen may be prepared by reacting an isothiocyanate of formula XII with an amino ester of formula V in an inert solvent to form an intermediate, thiourea compound and treating the thiourea compound with ethanolic hydrogen chloride or base at an elevated temperature. The above reaction scheme is shown below in Flow Diagram VIII.

FLOW DIAGRAM VIII

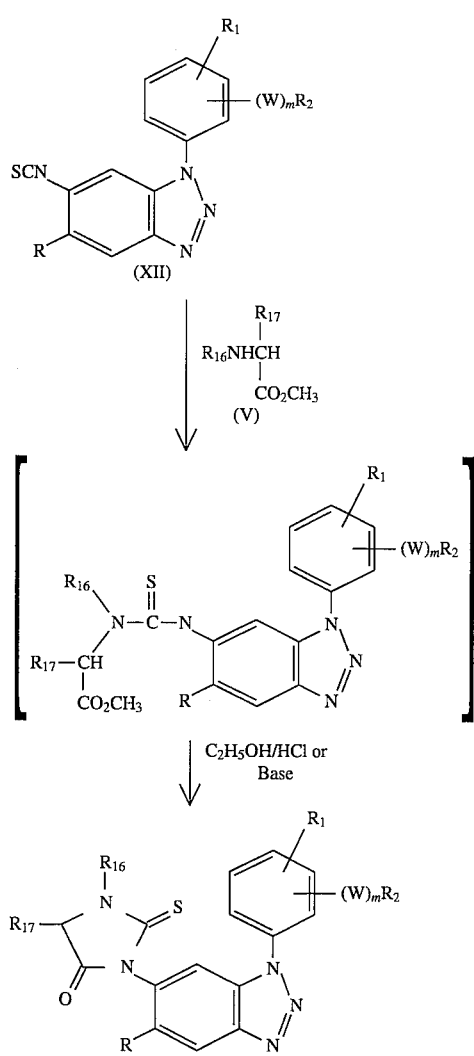

FLOW DIAGRAM IX

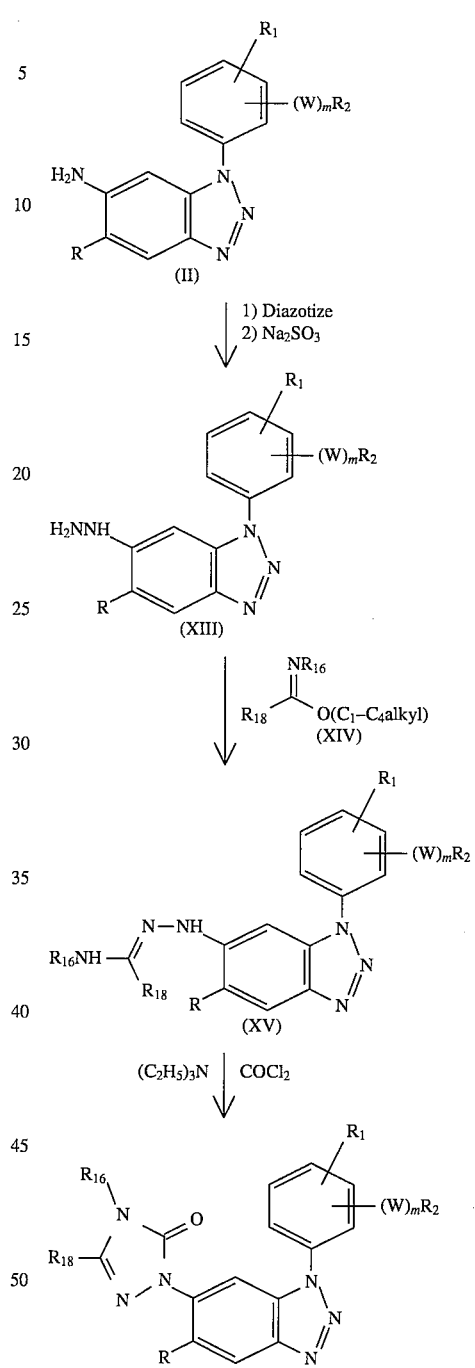

Formula I compounds wherein Q is Q5 and A and/or $A_1$ are sulfur may be prepared by treating a formula I compound wherein Q is Q5 and A and $A_1$ are oxygen with phosphorus pentasulfide or Lawesson's reagent in an inert solvent such as toluene, xylene or chloroform.

Formula I compounds wherein Q is Q4 may be prepared by diazotizing a 6-amino-1-(substituted phenyl)benzotriazole of formula II by standard methods to form an intermediate compound which is reduced with sodium sulfite to form a hydrazine of formula XIII. The hydrazine is then reacted with an imino ester of formula XIV to form an amidrazone of formula XV and reacting the amidrazone with phosgene or a suitable phosgene equivalent optionally in the presence of triethylamine to form the desired compound. The reactions are shown in Flow Diagram IX.

Compounds of formula I wherein Q is Q7 may be prepared by reacting a 6-amino-1-(substituted phenyl)benzotriazole of formula II with a β-aminoaldehyde of formula XVI in the presence of a base in an inert solvent to form an intermediate compound and reacting the intermediate compound with phosgene or a phosgene equivalent. The above reaction scheme is shown in Flow Diagram X.

FLOW DIAGRAM X

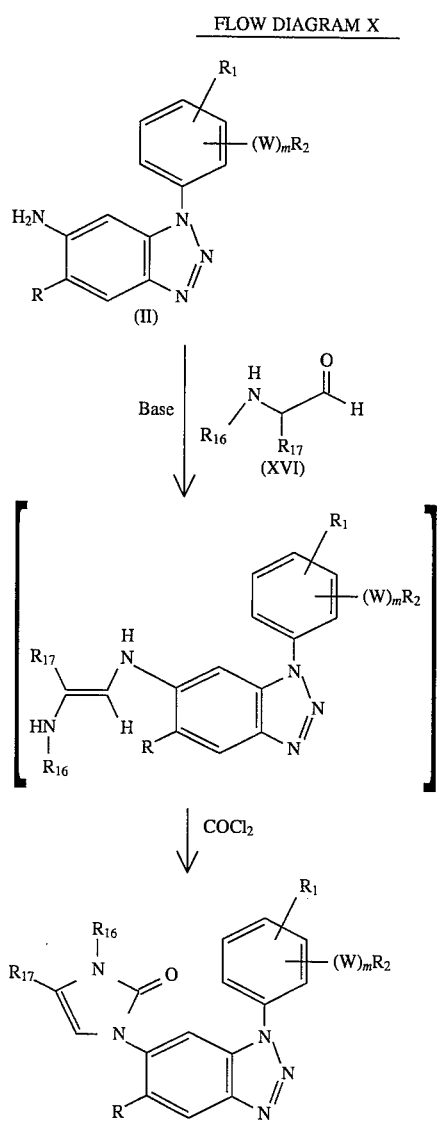

Formula I compounds wherein Q is Q8 and M is halogen may be prepared by reacting a hydrazine compound of formula XIII or its hydrochloride salt with a 2-alkoxycarbonylalkanone of formula XVII optionally in the presence of a base such as triethylamine or sodium acetate in an inert solvent such as ethanol or toluene to form a 2,3-dihydropyrazol-3-one of formula XVIII and halogenating the formula XVIII compound with phosphorus oxychloride or phosphorus oxybromide. The reactions are shown in Flow Diagram XI.

FLOW DIAGRAM XI

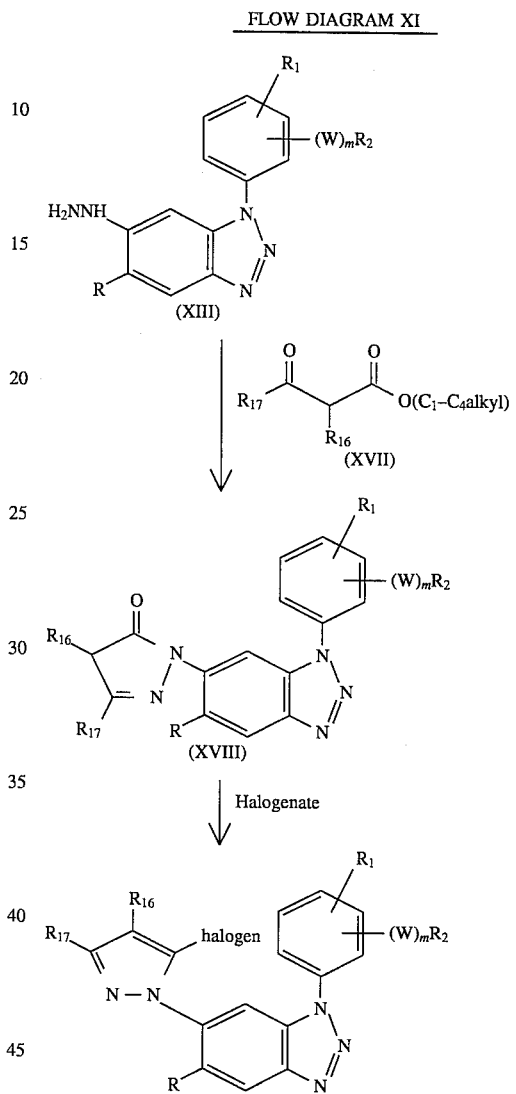

Formula I compounds wherein Q is Q8 and M is $C_1$–$C_3$ alkyl may be prepared by reacting a hydrazine compound of formula XIII with a 1,3-diketone of formula XIX optionally in the presence of a base in an inert solvent. The reaction is shown below in Flow Diagram XII.

FLOW DIAGRAM XII

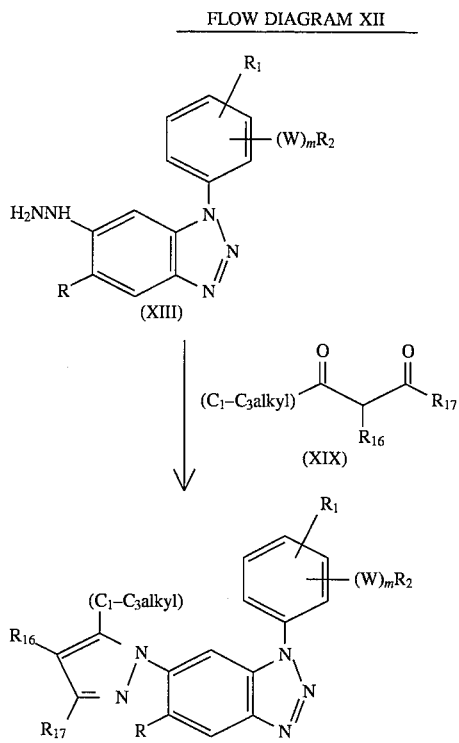

Formula I compounds wherein Q is Q9 may be prepared by diazotizing a 6-amino-1-(substituted phenyl)benzotriazole of formula II to form an intermediate diazonium salt and reacting the intermediate salt in situ with a β-aminoacid of formula XX in the presence of triethylamine. The reaction scheme is shown below in Flow Diagram XIII.

FLOW DIAGRAM XIII

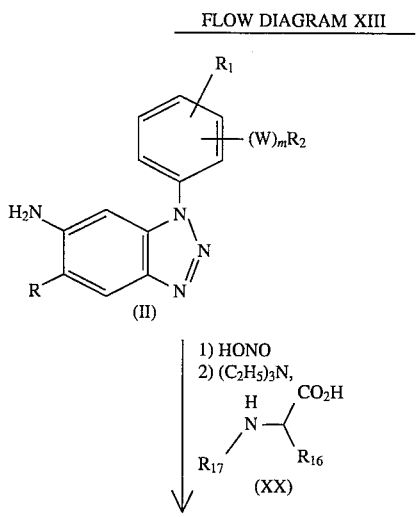

-continued
FLOW DIAGRAM XIII

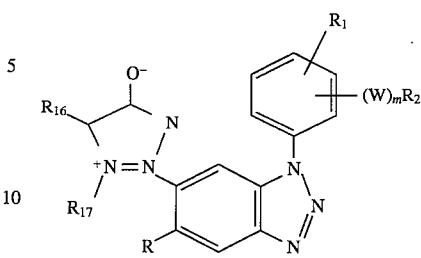

Compounds of formula I wherein Q is Q10 may be prepared by reacting a hydrazine of formula XIII with an acyl halide of formula XXI in the presence of a base such as triethylamine or pyridine to form an acyl hydrazide of formula XXII and reacting the acyl hydrazide with trichloromethyl chloroformate, phosgene or a suitable phosgene equivalent optionally in the presence of triethylamine. The reaction scheme is shown below in Flow Diagram XIV.

FLOW DIAGRAM XIV

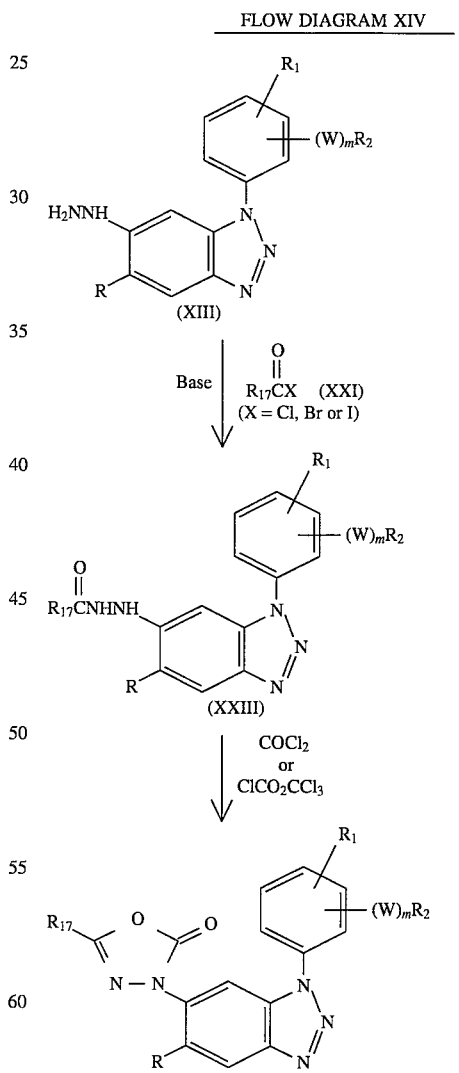

Formula I compounds wherein Q is Q11, A is sulfur, $A_1$ is oxygen and Z is CH may be prepared by reacting an isothiocyanate of formula XII with an amine of formula XXIII to form a thiourea of formula XXIV and reacting the thiourea with an α-halocarbonyl halide of formula XXV in the presence of a base. The reactions are shown in Flow Diagram XV.

FLOW DIAGRAM XV

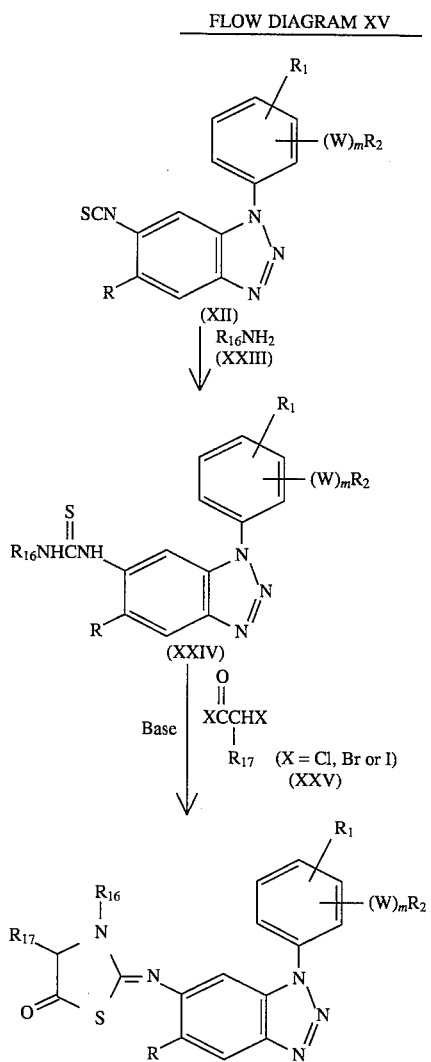

Formula I compounds wherein Q is Q11, A is sulfur, $A_1$ is oxygen and Z is nitrogen may be prepared by reacting an isothiocyanate of formula XII with a substituted hydrazine of formula XXVI to form an intermediate compound of formula XXVII and reacting the intermediate compound with phosgene or a suitable phosgene equivalent in the presence of a base such as triethylamine. The reaction sequence is shown in Flow Diagram XVI.

FLOW DIAGRAM XVI

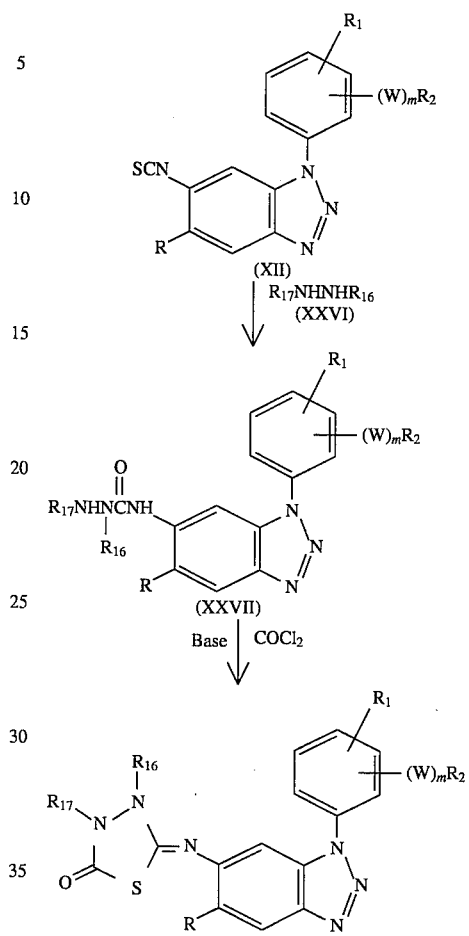

Compounds of formula I wherein Q is Q11, A and $A_1$ are oxygen and Z is CH may be prepared by reacting an isocyanate of formula III with an amine of formula XXIII to form a urea of formula XXVIII, dehydrating the urea to form a carbodiimide of formula XXIX, reacting the carbodiimide with an α-halocarbonyl halide of formula XXV to form a haloamidine of formula XXX, hydrolyzing the haloamidine with aqueous acid to form an acylurea, heating the acylurea in situ to form an O-acylurea of formula XXXI and reacting the O-acylurea with a base such as triethylamine. The above reaction sequence is shown below in Flow Diagram XVII.

FLOW DIAGRAM XVII

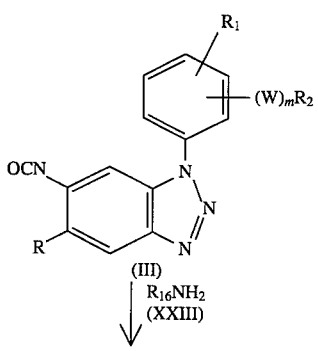

-continued
FLOW DIAGRAM XVII

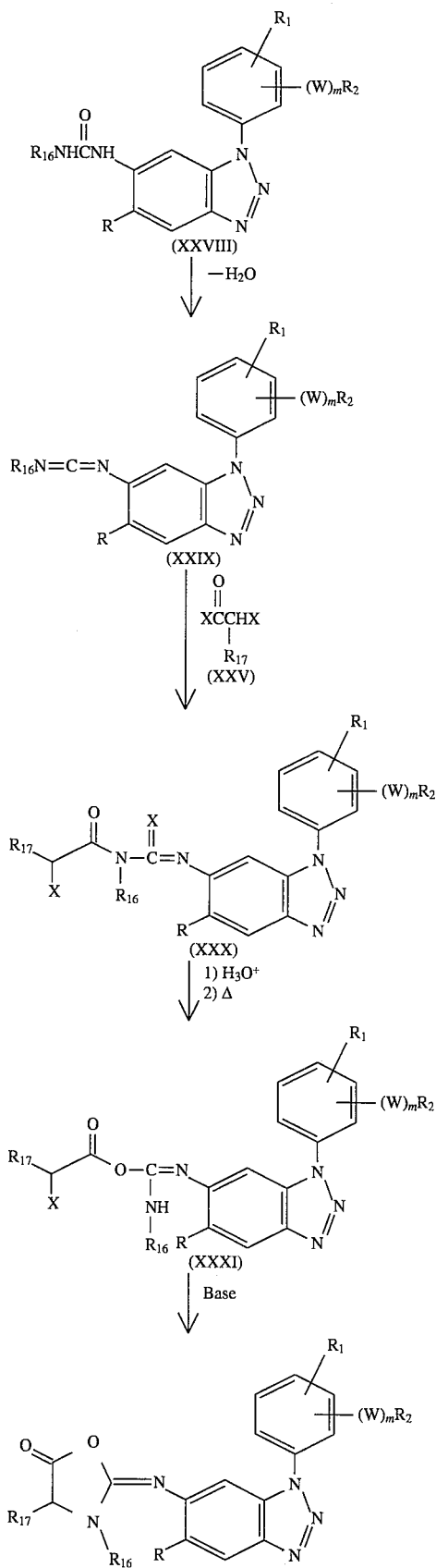

Formula I compounds wherein Q is Q12 and A and $A_1$ are oxygen may be prepared by reacting a 6-amino-1-(substituted phenyl)benzotriazole of formula II with an anhydride of formula XI to form an acid-amide of formula XXXII and dehydrating the acid-amide with a dehydrating agent such as 1,3-dicyclohexylcarbodiimide. The reaction scheme is shown below in Flow Diagram XVIII.

FLOW DIAGRAM XVIII

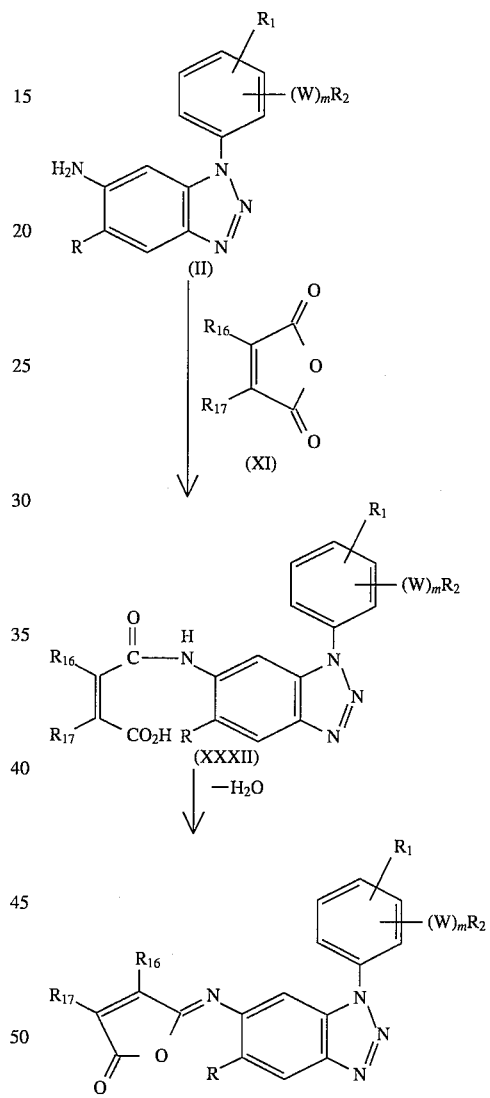

Compounds of formula I wherein Q is Q12, A is sulfur and $A_1$ is oxygen may be prepared by reacting an acid-amide of formula XXXII with phosphorus pentasulfide or Lawesson's reagent followed by base to form an acid-thioamide of formula XXXIII and dehydrating the acid-thioamide with a dehydrating agent such as 1,3-dicyclohexylcarbodiimide. The reactions are shown in Flow Diagram XIX.

FLOW DIAGRAM XIX

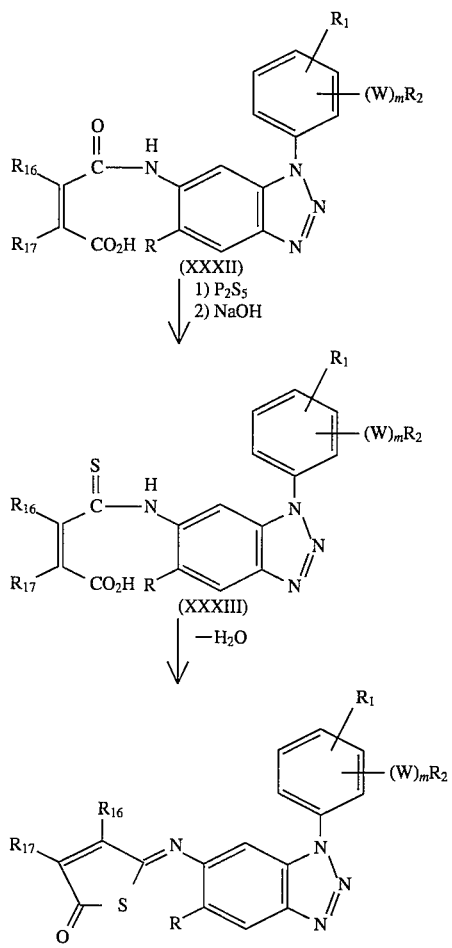

Certain formula I compounds wherein Q is Q13 may be prepared by reacting a thiourea of formula XXIV with iodomethane to form an isothiourea of formula XXXIV and reacting the isothiourea with a chloro-oxime of formula XXXV. The reaction scheme is shown in Flow Diagram XX.

FLOW DIAGRAM XX

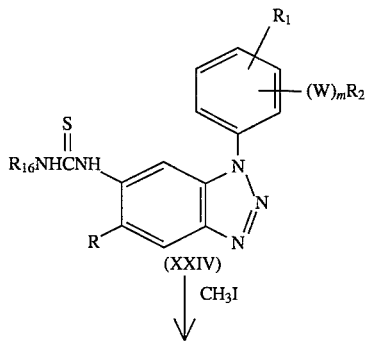

-continued
FLOW DIAGRAM XX

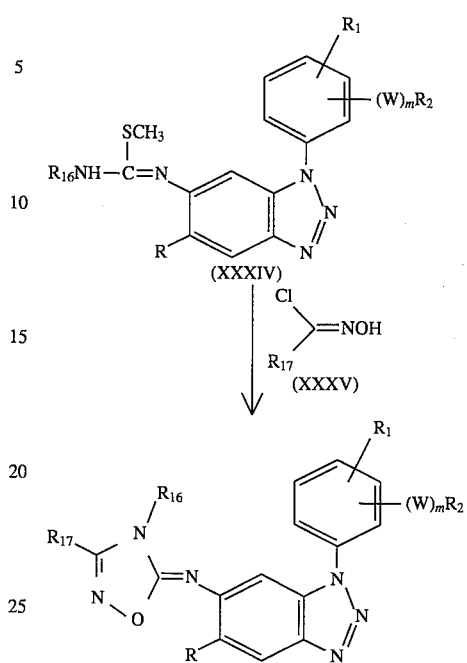

Compounds of formula I wherein Q is Q14 may be prepared by reacting a 6-amino-1-(substituted phenyl)benzotriazole of formula II with ethyl chloroformate to form a carbamate of formula XXXVI and reacting the carbamate with a hydroxy ester of formula XXXVII at an elevated temperature with removal of ethanol. The reaction sequence is shown in Flow Diagram XXI.

FLOW DIAGRAM XXI

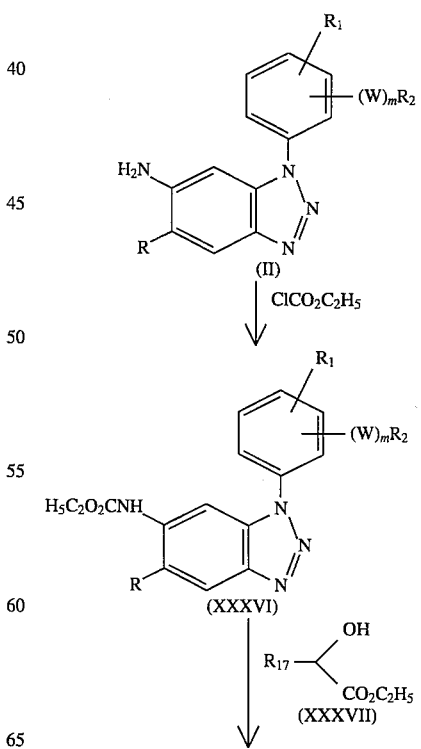

-continued
FLOW DIAGRAM XXI

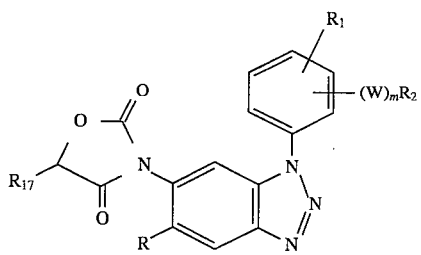

Alternatively, compounds of formula I wherein Q is Q14 may be prepared by reacting an isocyanate of formula III with a hydroxy ester of formula XXXVII to form an intermediate compound of formula XXXVIII and reacting the intermediate compound with a base such as sodium acetate in an inert solvent such as toluene. The reaction scheme is shown below in Flow Diagram XXII.

FLOW DIAGRAM XXII

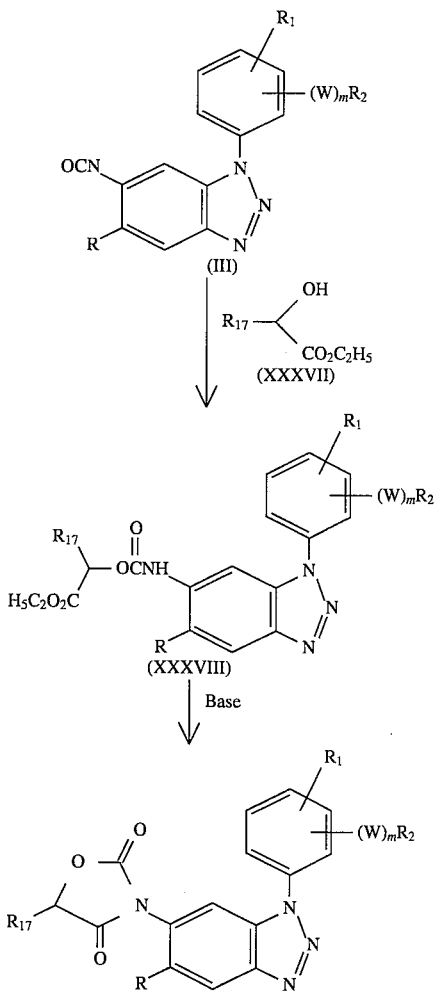

Formula I compounds wherein Q is Q15 may be prepared by reacting an isocyanate of formula III with an α-amino-α,β-unsaturated ester of formula XXXIX to form a urea of formula XL and reacting the urea with a base such as sodium acetate in an inert solvent such as toluene at an elevated temperature. The reactions are shown in Flow Diagram XXIII.

FLOW DIAGRAM XXIII

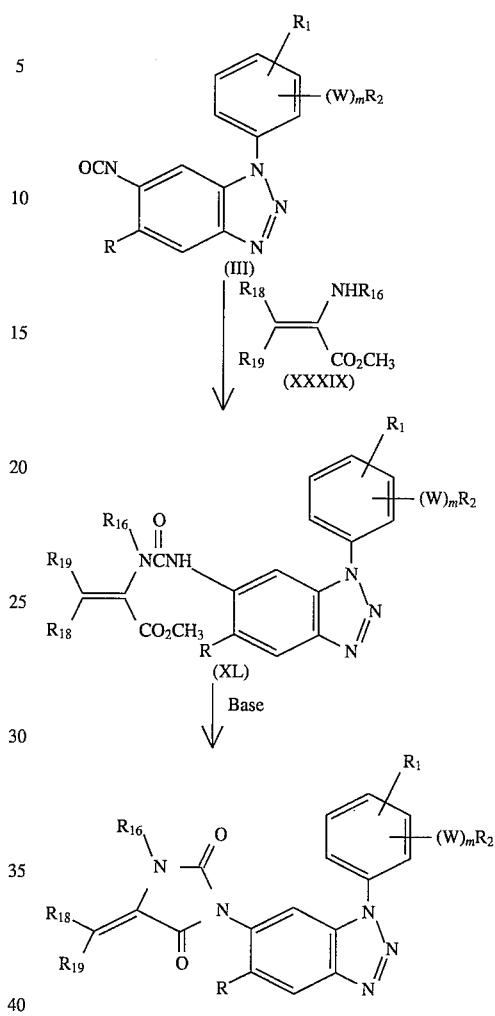

Alternatively, formula I compounds wherein Q is Q15 may be prepared by reacting an isocyanate of formula III with an amino acid of formula XLI to form a urea of formula XLII, reacting the urea with aqueous acid to form a hydantoin of formula XLIII and reacting the hydantoin with an acetal of formula XLIV. The reaction scheme is shown below in Flow Diagram XXIV.

FLOW DIAGRAM XXIV

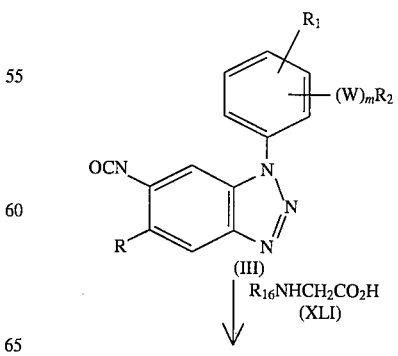

-continued
FLOW DIAGRAM XXIV

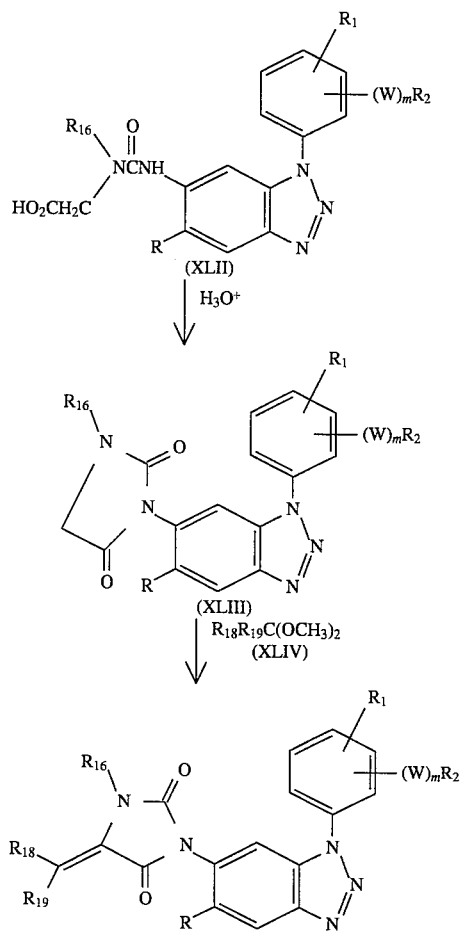

Compounds of Formula I wherein Q is Q16 may be prepared by reacting an isocyanate of formula III with a hydroxy alkenoate of formula XLV in the presence of a base such as triethylamine. The reaction is shown in Flow Diagram XXV.

FLOW DIAGRAM XXV

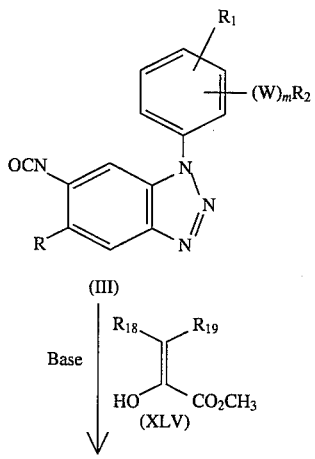

-continued
FLOW DIAGRAM XXV

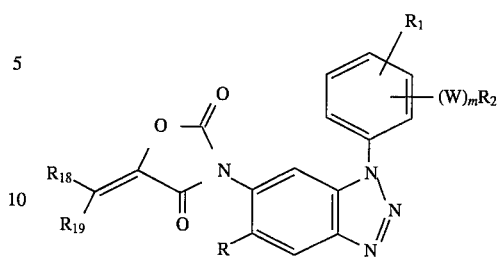

Formula I compounds wherein Q is Q17 may be prepared by reacting a formula I compound wherein Q is Q6 with a Grignard Reagent of formula XLVI in a solvent such as diethyl ether or tetrahydrofuran at an elevated temperature to form an intermediate compound of formula XLVII and reacting the intermediate compound with potassium bisulfate at an elevated temperature. The reaction scheme is shown in Flow Diagram XXVI.

FLOW DIAGRAM XXVI

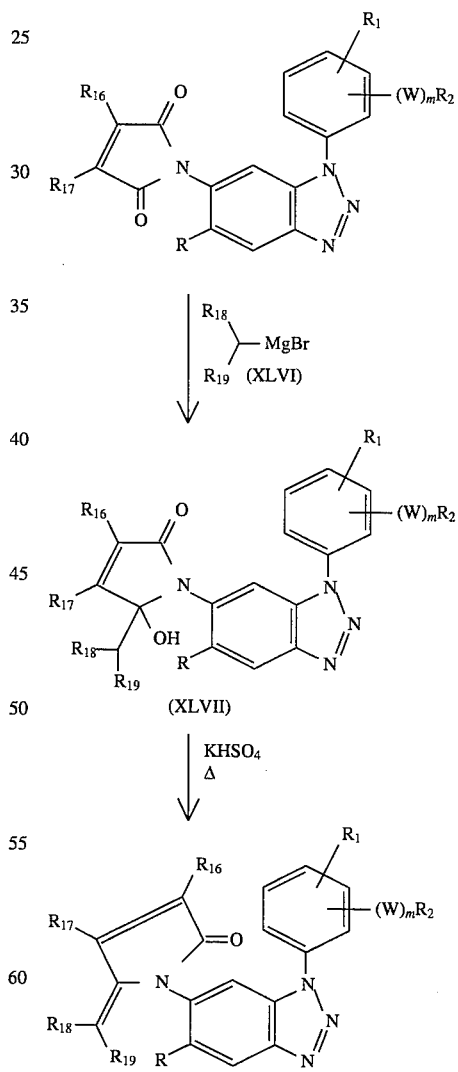

Formula I compounds wherein Q is Q18 may be prepared by reacting a 6-amino-1-(substituted phenyl)benzotriazole of formula II with an anhydride of formula XLVIII in acetic anhydride with a catalytic amount of sodium acetate at an elevated temperature, in acetic acid at an elevated temperature or in xylene with a catalytic amount of p-toluene sulfonic acid at an elevated temperature. The reaction is shown below in Flow Diagram XXVII.

FLOW DIAGRAM XXVII

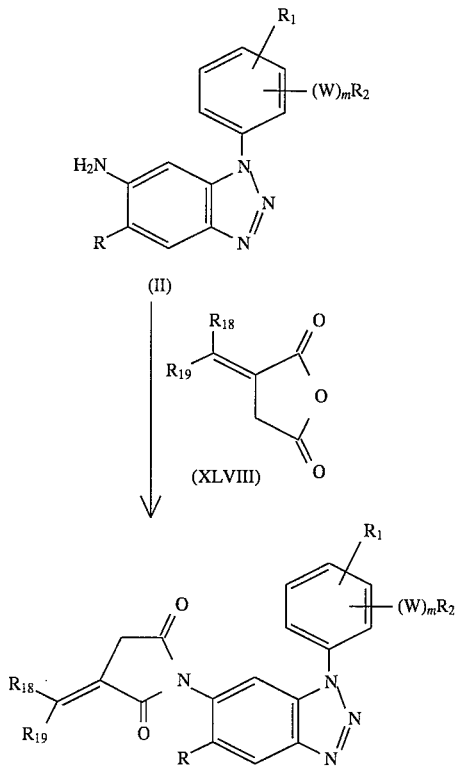

Alternatively, formula I compounds wherein Q is Q18 may be prepared by reacting a 6-amino-1-(substituted phenyl)benzotriazole of formula II with a diacid of formula XLIX in xylene at reflux. The reaction scheme is shown below in Flow Diagram XXVIII.

FLOW DIAGRAM XXVIII

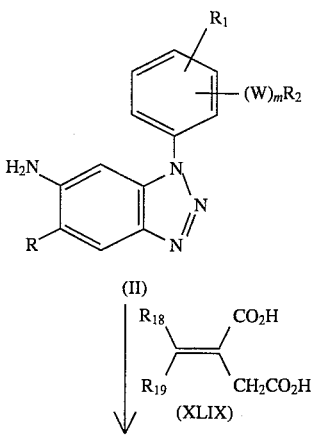

-continued
FLOW DIAGRAM XXVIII

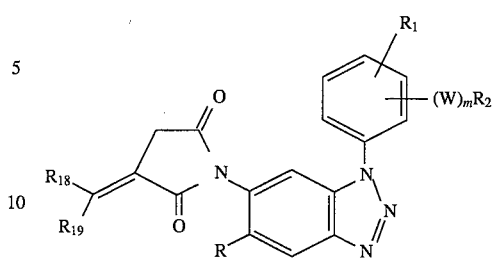

Compounds of formula I wherein Q is Q19 may be prepared by reacting a 6-amino-1-(substituted phenyl)benzotriazole of formula II with ethyl malonyldiurethane and sodium nitrite in acetic acid with a catalytic amount of concentrated hydrochloric acid to form a hydrazone of formula L, cyclizing the hydrazone with base to form a triazinedione of formula LI and decarboxylating the triazinedione with mercaptoacetic acid at an elevated temperature and optionally alkylating the formula I compound wherein Q is Q19 and $R_{16}$ is hydrogen with an alkyl halide and a base such as sodium hydride. The reaction scheme is shown in Flow Diagram XXIX.

FLOW DIAGRAM XXIX

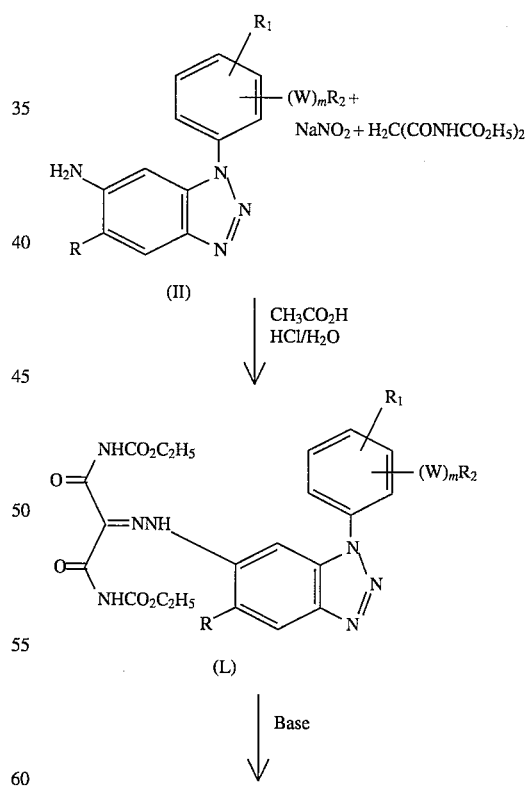

FLOW DIAGRAM XXIX -continued

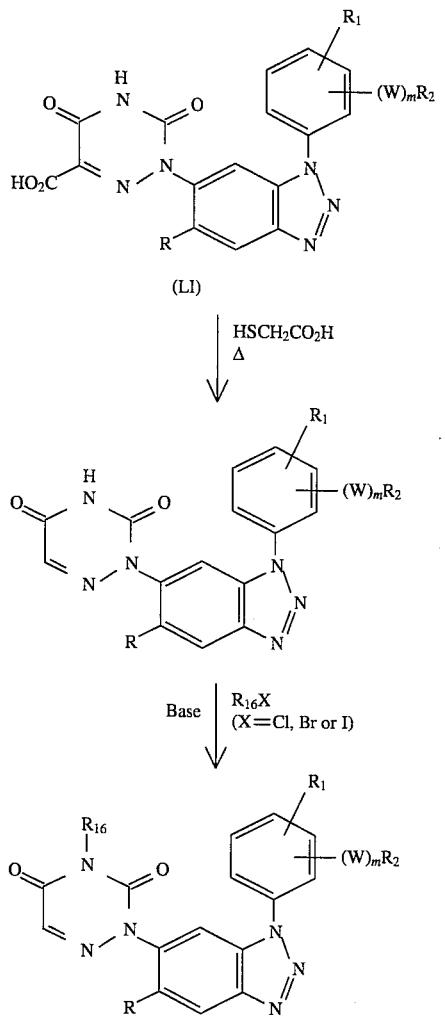

FLOW DIAGRAM XXX

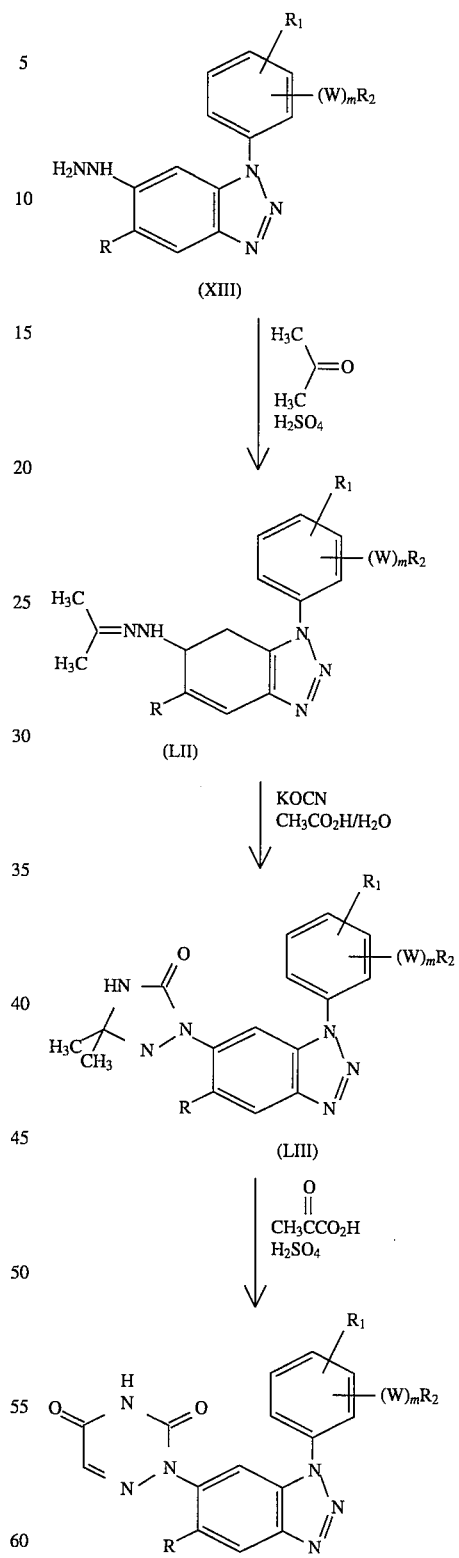

Alternatively, compounds of formula I wherein Q is Q19 and $R_{16}$ is hydrogen may be prepared by reacting a hydrazine of formula XIII with acetone in a sulfuric acid solution to form a hydrazone of formula LII, reacting the hydrazone with potassium cyanate in an acetic acid solution to form a triazolidine of formula LIII and reacting the triazolidine with pyruvic acid and sulfuric acid. The reaction sequence is shown below in Flow Diagram XXX.

Formula I compounds wherein Q is Q20 may be prepared by reacting an isocyanate of formula III with an amino ester of formula LIV in the presence of a base such as sodium hydride to form an intermediate compound of formula LV and cyclizing the intermediate compound with acid and optionally alkylating the formula I compound wherein Q is Q20 and $R_{20}$ is hydrogen with a $C_1$–$C_3$alkyl halide and a base such as sodium hydride. The reaction scheme is shown in Flow Diagram XXXI.

FLOW DIAGRAM XXXI

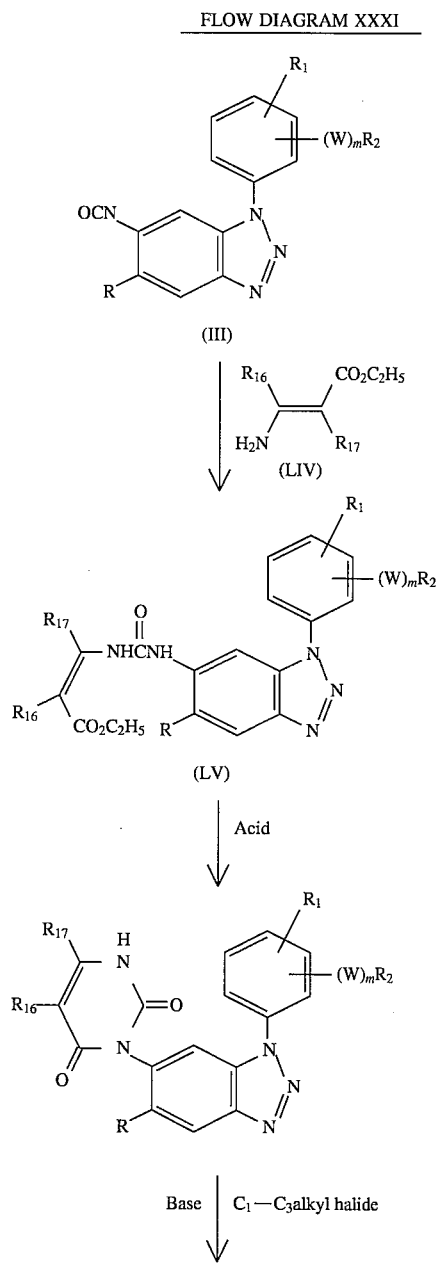

-continued
FLOW DIAGRAM XXXI

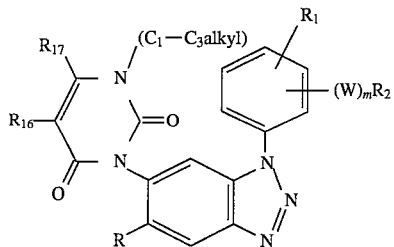

Compounds of formula I wherein Q is Q21 may be prepared by reacting a formula I compound wherein Q is Q20 and $R_{16}$ is hydrogen with sodium borohydride. The reaction is shown below in Flow Diagram XXXII.

FLOW DIAGRAM XXXII

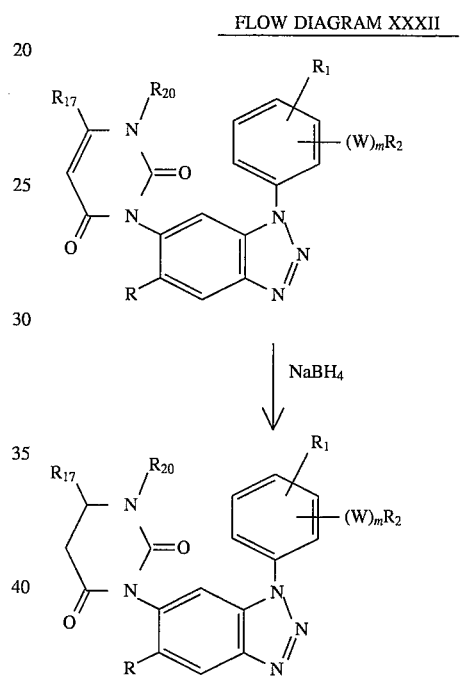

Alternatively, compounds of formula I wherein Q is Q21 may be prepared by reacting an amine of formula LVI with an α,β-unsaturated ester of formula LVII to form an amino ester of formula LVIII and reacting the amino ester with an isocyanate of formula III followed by heating in an acidic methanol solution. The reaction sequence is shown below in Flow Diagram XXXIII.

FLOW DIAGRAM XXXIII

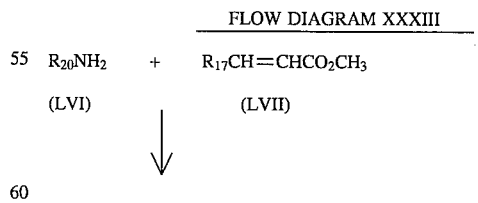

-continued
FLOW DIAGRAM XXXIII

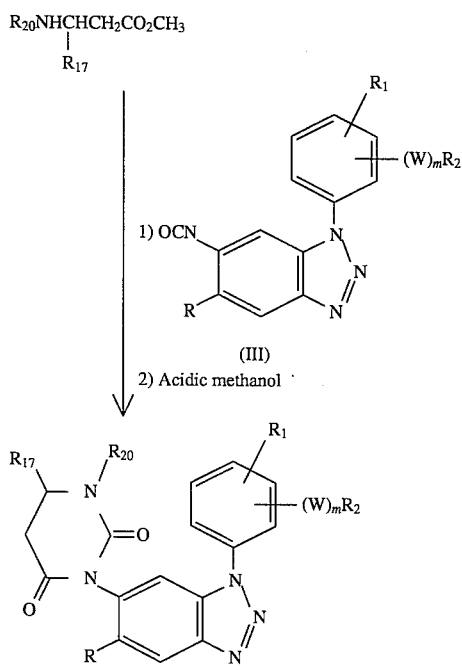

Compounds of formula I wherein Q is Q22 may be prepared by reacting a hydrazine of formula XIII with a β-carbonyl aldehyde of formula LVIII followed by cyclization under acidic conditions to form a dihydropyridazinone of formula LIX and dehydrogenating the dihydropyridazinone with chloranil or 2,3-dichloro-5,6-dicyanobenzoquinone (DDQ) in an inert solvent such as dioxane or toluene at an elevated temperature. The reaction scheme is shown in Flow Diagram XXXIV.

FLOW DIAGRAM XXXIV

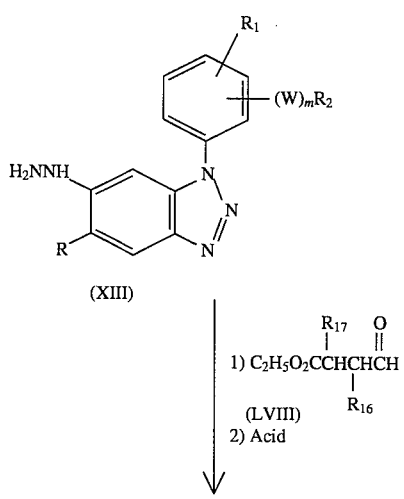

-continued
FLOW DIAGRAM XXXIV

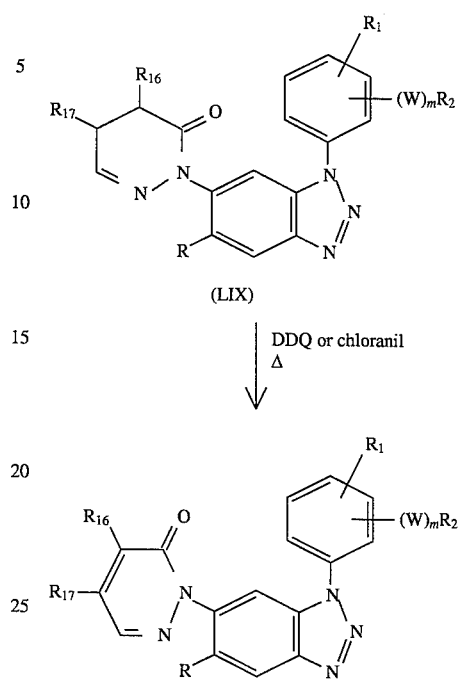

Certain 6-amino-1-(substituted phenyl)benzotriazole compounds of formula II may be prepared by reacting a 3-fluoroaniline compound of formula LX with acetic anhydride in the presence of an acid such as sulfuric acid to form a 3'-fluoroacetanilide compound of formula LXI, reacting the 3'-fluoroacetanilide compound with nitric acid to form a 3'-fluoro-4'-nitroacetanilide compound of formula LXII, reacting the 3'-fluoro-4'-nitroacetanilide with a substituted aniline of formula LXIII to form a (5-acetamido-2-nitroanilino)phenyl compound of formula LXIV, reducing the (5-acetamido-2nitroanilino)phenyl compound with iron in the presence of an acid such as acetic acid to form a (5-acetamido-2aminoanilino)phenyl compound of formula LXV, cyclyzing the (5-acetamido-2-aminoanilino)-phenyl compound with sodium nitrite in an acetic acid solution to form a 6-acetamido-1-(substituted phenyl)-benzotriazole of formula LXVI and treating the 6-acetamido-1-(substituted phenyl)benzotriazole compound with aqueous acid to form the desired formula II compound. The above reaction scheme is shown below in Flow Diagram XXXV.

FLOW DIAGRAM XXXV

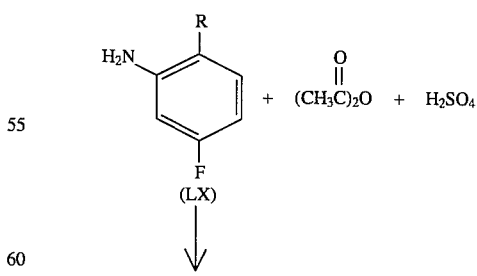

-continued
FLOW DIAGRAM XXXV

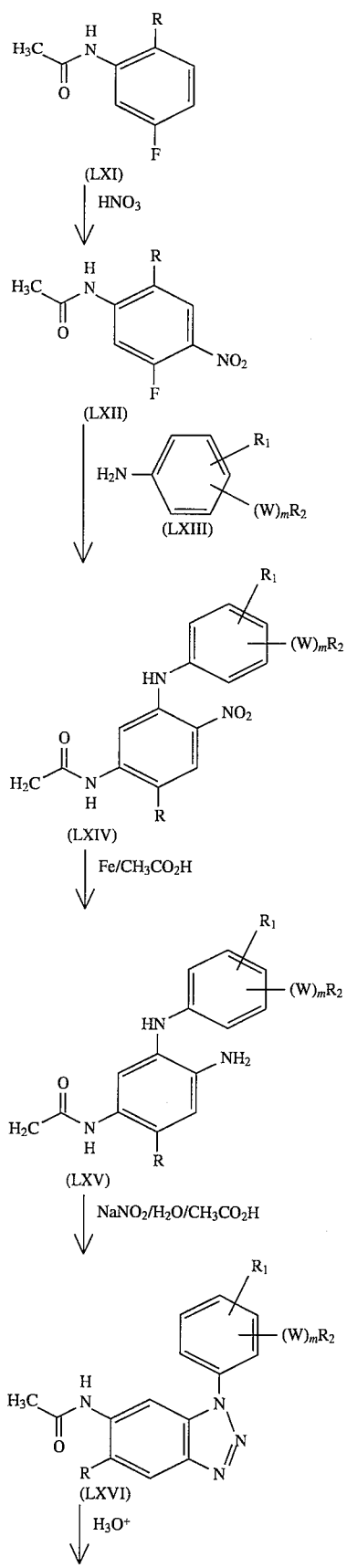

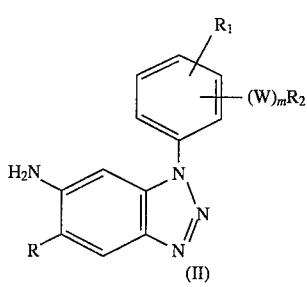

Compounds of formula I wherein $R_5$ is $NR_{11}R_{12}$ may be prepared using standard procedures such as hydrolyzing the appropriate ester of formula LXVII in the presence of a base to form the corresponding acid, reacting the acid with thionyl chloride to give the acid chloride of formula LXVIII and reacting the formula LXVIII acid chloride with an amine of formula LXIX optionally in the presence of a base to give the desired product. The reaction is shown below in Flow Diagram XXXVI.

FLOW DIAGRAM XXXVI

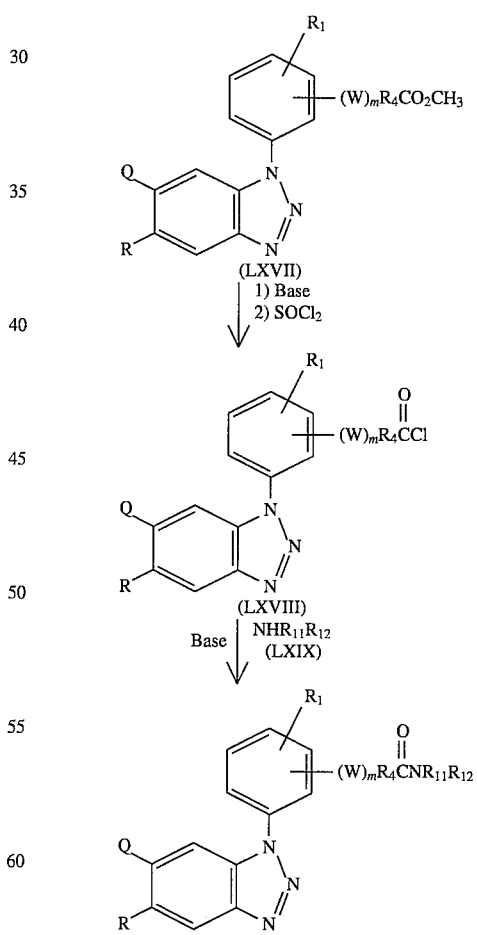

Similarly, compounds of formula I wherein $R_5$ is $N(R_6)SO_2R_9$ may be prepared by reacting an acid chloride of formula LXVIII with a sulfonamide of formula LXX optionally in the presence of a base. The reaction scheme is shown below in Flow Diagram XXXVII.

FLOW DIAGRAM XXXVII

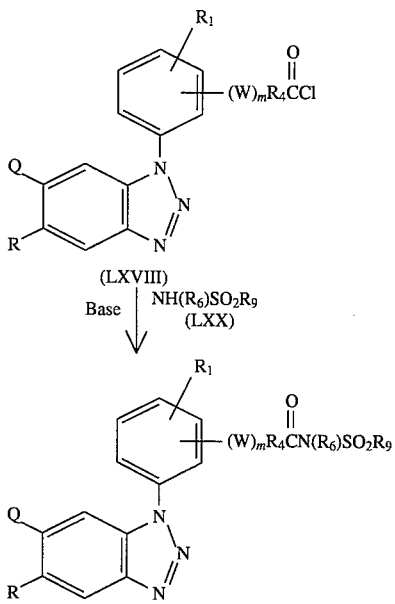

Using the formula LXVIII acid chloride, formula I compounds wherein V is $C(O)R_6$ may also be prepared as shown below in Flow Diagram XXXVIII.

FLOW DIAGRAM XXXVIII

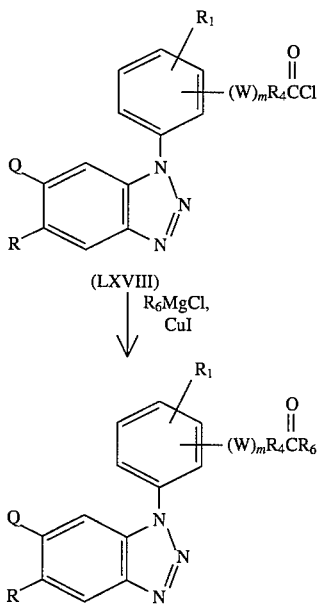

Formula I compounds wherein W is oxygen, m is 1 and V is hydrogen may also be prepared by reacting a formula I compound wherein W is oxygen, m is 1 and V is methyl with boron tribromide as shown in Flow Diagram XXXIX.

FLOW DIAGRAM XXXIX

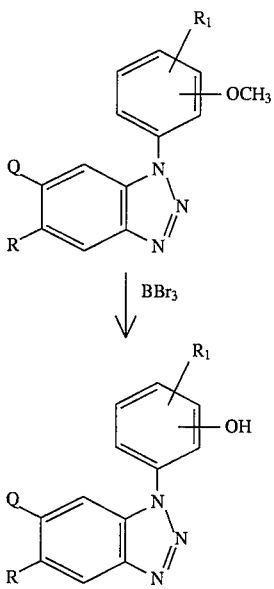

Using the formula I compound wherein W is oxygen, m is 1 and V is hydrogen, formula I compounds wherein W is oxygen, m is 1 and V is $CH(OR_8)_2$, CHO or $HC=NOR_7$ may also be prepared as shown below in Flow Diagram XL.

FLOW DIAGRAM XL

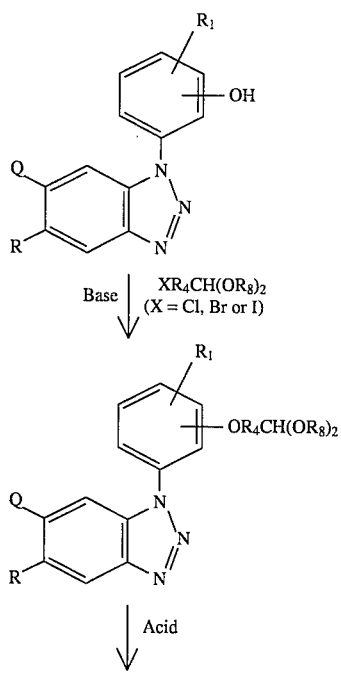

FLOW DIAGRAM XL -continued

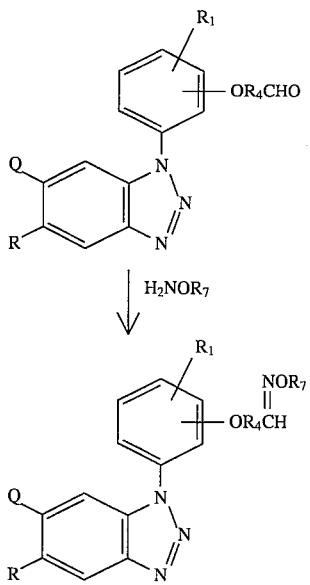

Compounds of formula I wherein V is cyano may be prepared by reacting the formula I compound wherein W is oxygen, m is 1 and V is hydrogen with a haloalcohol of formula LXXI to give the alcohol of formula LXXII, reacting the formula LXXII alcohol with phosphorus oxychloride to give the chloride compound of formula LXXIII and reacting the chloride compound with potassium cyanide to obtain the desired compound. The reaction sequence is shown below in Flow Diagram XLI.

FLOW DIAGRAM XLI

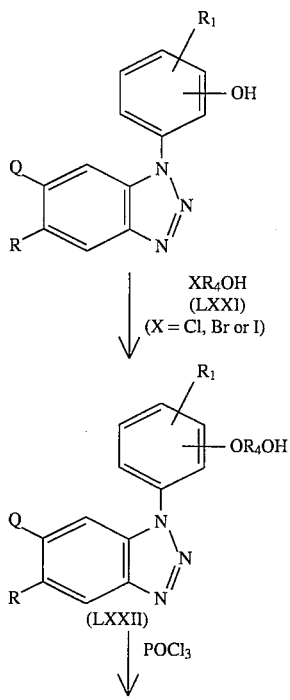

FLOW DIAGRAM XLI -continued

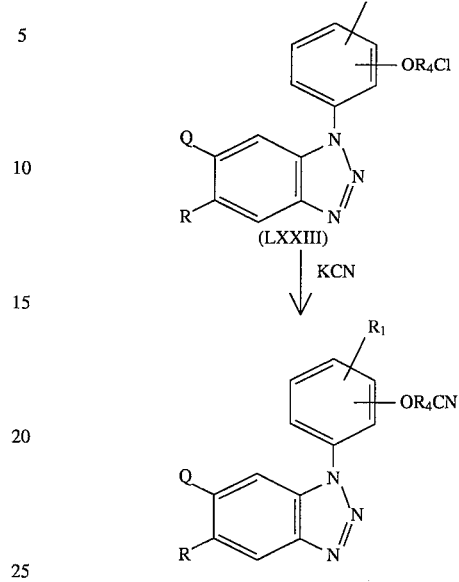

Using the formula LXXII alcohol, formula I compounds wherein $R_6$ is $C_1$–$C_4$alkyl optionally substituted with $C_1$–$C_4$alkoxy may be prepared as shown below in Flow Diagram XLII.

FLOW DIAGRAM XLII

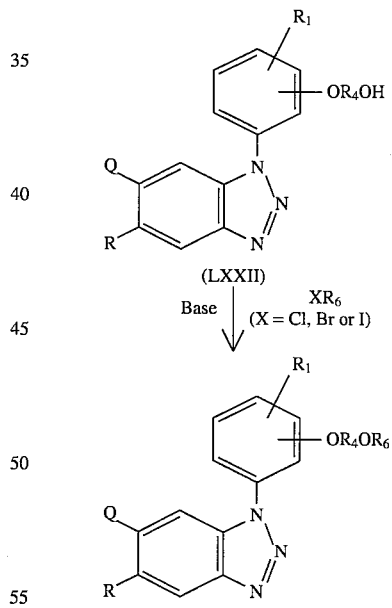

Similarly, compounds of formula I wherein $R_7$ is $C_1$–$C_4$alkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups may be prepared by reacting a formula LXXII alcohol with an acid chloride of formula LXXIV in the presence of a base. The reaction is shown in Flow Diagram XLIII.

FLOW DIAGRAM XLIII

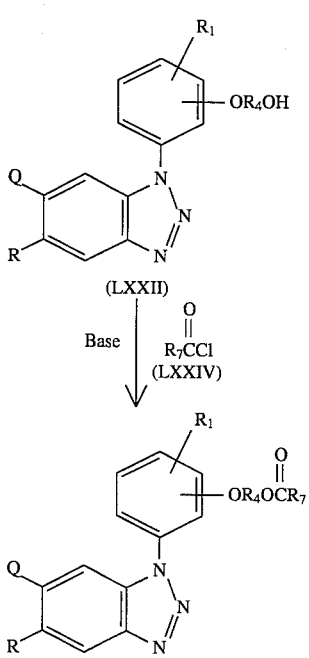

Formula I compounds wherein V is $C_2$–$C_6$alkenyl substituted with one $CO_2R_7$ group or $C_2$–$C_6$alkynyl substituted with one $CO_2R_7$ group may be prepared by reacting the formula I compound wherein W is oxygen, m is 1 and V is hydrogen with a halide compound of formula LXXV in the presence of a base as shown in Flow Diagram XLIV.

FLOW DIAGRAM XLIV

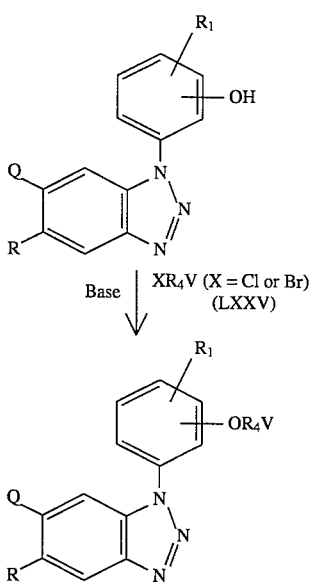

Formula I compounds wherein $R_5$ is hydroxy may be prepared by hydrolyzing a formula LXVII ester in the presence of a base followed by treatment with acid as shown in Flow Diagram XLV.

FLOW DIAGRAM XLV

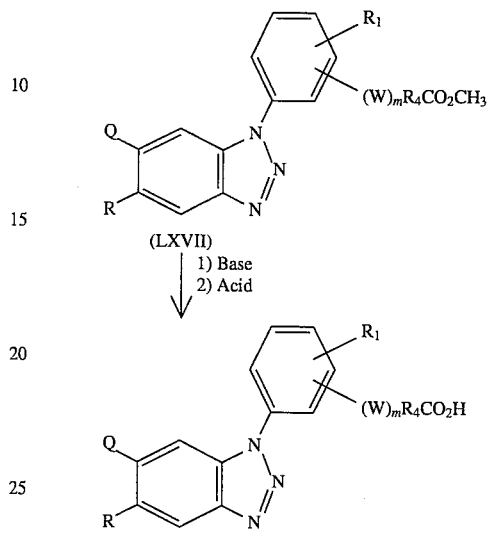

Compounds of formula I wherein $R_{10}$ is an alkali metal, alkaline earth metal, manganese, copper, zinc, cobalt, silver, nickel, ammonium or organic ammonium cation may be prepared from formula I compounds wherein $R_5$ is hydroxy by standard procedures known to those skilled in the art.

The present invention also provides a method for the preparation of certain compounds of this invention having the structural formula

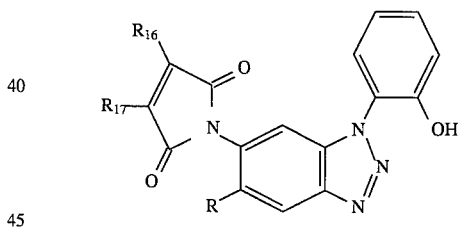

wherein

R is hydrogen, halogen or $C_1$–$C_4$alkyl; and $R_{16}$ and $R_{17}$ are each independently hydrogen, $C_1$–$C_6$alkyl optionally substituted with one or more halogen atoms, or $C_3$–$C_6$cycloalkyl optionally substituted with one or more halogen atoms; and when $R_{16}$ and $R_{17}$ are taken together with the atoms to which they are attached, they may form a ring in which $R_{16}R_{17}$ is a $C_2$–$C_5$alkylene group optionally substituted with one to three methyl groups or one or more halogen atoms, which comprises: reducing a compound having the structural formula LXXVI

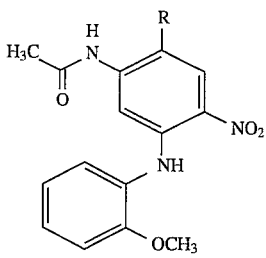
(LXXVI)

wherein R is as described above with iron, preferably iron powder, in the presence of an organic acid such as acetic acid, optionally in a solvent, to form a compound having the structural formula LXXVII

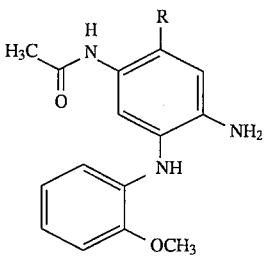
(LXXVII)

wherein R is as described above, cyclizing the formula LXXVII compound with sodium nitrite in the presence of an organic acid such as acetic acid optionally in the presence of a solvent to form a compound having the structural formula LXXVIII

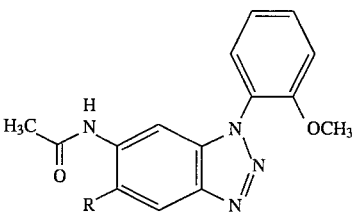
(LXXVIII)

wherein R is as described above, reacting the formula LXXVIII compound with an aqueous acid such as hydrochloric acid to form a compound having the structural formula LXXIX

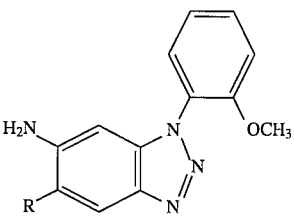
(LXXIX)

wherein R is as described above, reacting the formula LXXIX compound with an anhydride compound having the structural formula

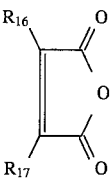

wherein $R_{16}$ and $R_{17}$ are as described above preferably at an elevated temperature to form a compound having the structural formula LXXX

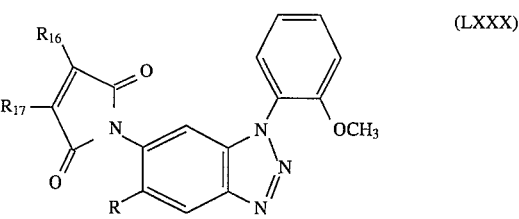
(LXXX)

wherein $R_{16}$ and $R_{17}$ are as described above, and reacting the formula LXXX compound with boron tribromide optionally in the presence of a solvent.

The thus-prepared compounds are useful as herbicidal agents and are also useful in the preparation of other compounds of formula I by using essentially the same procedures as described in Flow Diagrams XL, XLI and XLIV.

The heterocyclyl-1-(substituted phenyl)benzotriazole compounds of the present invention are effective herbicidal agents useful for the control of a wide variety of undesirable plant species. Those compounds are effective for controlling weeds native to both dry land and wet land areas. The compounds are also useful as aquatic herbicides and are effective in controlling the above-said plants when applied to the foliage thereof or to soil or water containing seeds or other propagating organs thereof such as stolons, tubers or rhizomes, at rates of from about 0.016 kg/ha to 4 kg/ha and preferably from about 0.05 kg/ha to 2 kg/ha.

The compounds of this invention are useful as broad spectrum herbicides. However, certain compounds of this invention are selective in crops such as soybeans, corn, rice, cotton, sunflower, barley and wheat.

The compounds of the present invention are particularly useful for the preemergence, selective control of undesirable plant species in the presence of soybeans, corn, rice, cotton, sunflower, barley and wheat. And when applied postemergence, the compounds of the present invention control undesirable plant species at low application rates with safety on soybeans and corn.

While the formula I compounds of this invention are effective for controlling undesirable plant species when employed alone, they may also be used in combination with other biological chemicals, including other herbicides.

The heterocyclyl-1-(substituted phenyl)benzotriazole compounds of this invention may be applied to undesirable plant species or to the soil or water containing seeds or other propagating organs thereof in the form of a solid or liquid herbicidal composition, comprising a herbicidally effective amount of the heterocyclyl-1-(substituted phenyl)benzotriazole compound dispersed or dissolved in an agronomically acceptable, inert solid or liquid carrier. The compositions may be applied as preemergence or postemergence treatments.

Advantageously, the formula I compounds may be formulated as emulsifiable concentrates, wettable powders, granular formulations, flowable concentrates and the like.

This invention further provides intermediate compounds which are useful in the preparation of the formula I compounds. The intermediate compounds have the structural formula

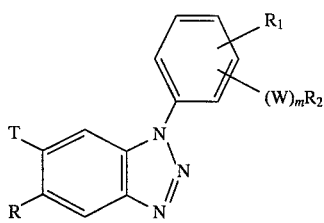

wherein

R, $R_1$, $R_2$, W and m are as described hereinabove for formula I; and

T is $NH_2$ or

Preferred intermediate compounds of the present invention are those wherein

R is hydrogen or halogen;

$R_1$ is hydrogen or $C_1$–$C_4$alkyl;

$R_2$ is V or $R_4$V;

$R_4$ is methylene optionally substituted with one or two halogen atoms, one $C_1$–$C_4$alkyl group or one $C_1$–$C_4$haloalkyl group;

V is hydrogen, halogen, $C(O)R_5$ or $C_2$–$C_6$alkynyl;

$R_5$ is OH or $OR_{10}$;

$R_{10}$ is $C_1$–$C_6$alkyl;

W is O;

m is an integer of 0 or 1; and

T is $NH_2$ or

The intermediate compounds may be prepared as shown in Flow Diagram XXXV hereinabove.

In order to facilitate a further understanding of the invention, the following examples are presented primarily for the purpose of illustrating more specific details thereof. The invention should not be deemed limited by the examples as the full scope of the invention is defined in the claims. The term NMR designates nuclear magnetic resonance spectroscopy.

EXAMPLE 1

Preparation of 2',5'-Difluoroacetanilide

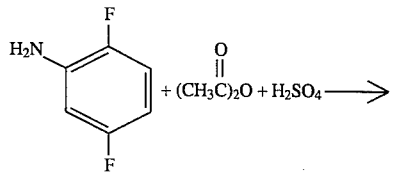

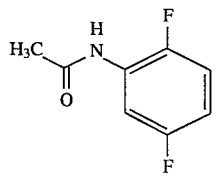

2,5-Difluoroaniline (100 g, 0.775 mol) is added dropwise to a mixture of concentrated sulfuric acid (4 drops) in acetic anhydride (250 mL) while maintaining the reaction mixture temperature below 15° C. After the addition is complete, the reaction mixture is stirred for one hour and filtered to obtain a solid. The solid is washed with diethyl ether and air dried to give the title product as a white solid, mp 124°–125° C.

EXAMPLE 2

Preparation of 2',5'-Difluoro-4'-nitroacetanilide

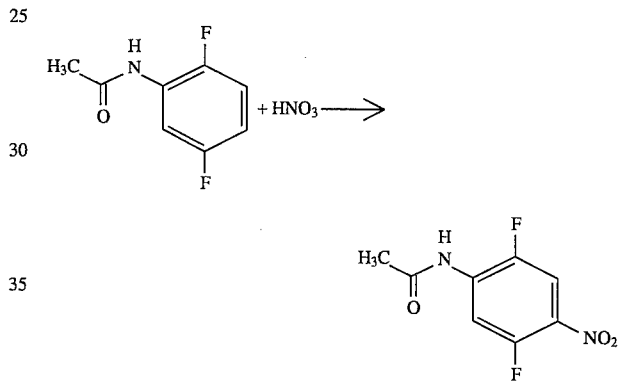

A mixture of nitric acid (21.85 mL) and sulfuric acid (28.5 mL) is added dropwise to a mixture of 2',5'-difluoroacetanilide (44.2 g, 0.281 mol) and acetic acid (19 mL) in sulfuric acid (190 mL) while maintaining the reaction mixture temperature below 10° C. After the addition is complete, the reaction mixture is stirred at 0° C. for one hour and poured onto cracked ice (2 L). The aqueous mixture is filtered to obtain a solid. The solid is air dried and recrystallized from ethanol to give the title product as a yellow, crystalline solid, mp 188°–189° C.

EXAMPLE 3

Preparation of Methyl 2-(4-nitrophenoxy)propionate

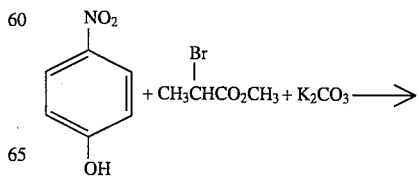

-continued

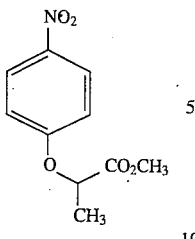

Methyl 2-bromopropionate (60.12 g, 0.36 mol) is added to a mixture of 4-nitrophenol (25 g, 0.18 mol) and potassium carbonate (49.75 g, 0.36 mol) in acetonitrile. The reaction mixture is refluxed for 18 hours, cooled and poured into water. The phases are separated and the aqueous phase is extracted with ethyl acetate. The organic phase and the organic extracts are combined, washed with water, dried over anhydrous sodium sulfate and concentrated in vacuo to give the title product as a white powder, mp 79°–80° C.

EXAMPLE 4

Preparation of Methyl 2-(4-aminophenoxy)propionate

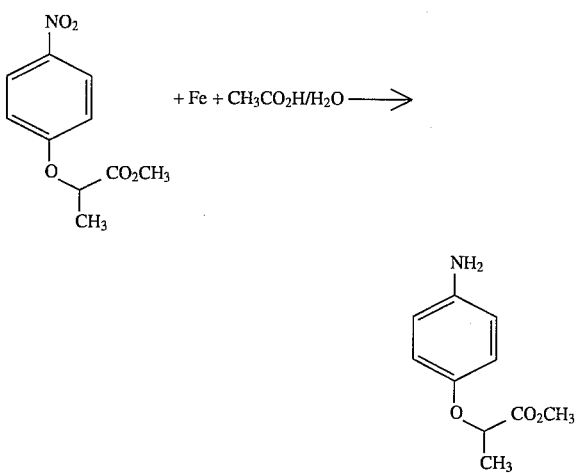

A solution of methyl 2-(4-nitrophenoxy)propionate (10 g, 0.044 mol) in ethyl acetate is added dropwise to a mixture of iron dust (7.37 g, 0.132 mol) in a 5% acetic acid solution at 65° C. The reaction mixture is stirred at 65° C. for 30 minutes, cooled to room temperature and filtered through diatomaceous earth. The resultant filtrate is diluted with water and extracted with ethyl acetate. The organic extracts are combined, washed sequentially with saturated sodium hydrogen carbonate solution and brine, dried over anhydrous sodium sulfate and concentrated in vacuo to give the title product as an oil which is identified by NMR spectral analyses.

EXAMPLE 5

Preparation of Methyl 2-[p-(5-acetamido-4-fluoro-2-nitroanilino)phenoxy] propionate

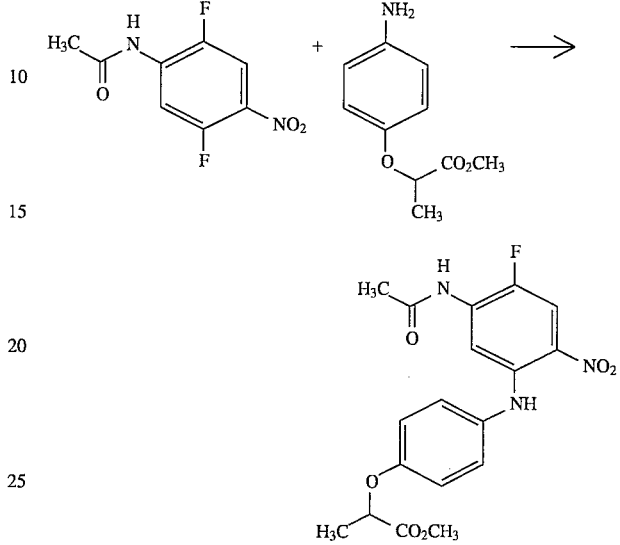

A mixture of 2',5'-difluoro-4'-nitroacetanilide (7.35 g, 0.034 mol) and methyl 2-(4-aminophenoxy)propionate (16.6 g, 0.085 mol) in dioxane is refluxed for 2 days, cooled to room temperature and poured into water. The resultant aqueous mixture is extracted with ethyl acetate and the organic extracts are combined, washed with brine, dried over anhydrous sodium sulfate and concentrated in vacuo to obtain a dark red gum. The gum is dissolved in hot diethyl ether and, after stirring briefly, an orange solid forms. The solid is collected via filtration and dried to give the title product as an orange solid, mp 126.5°–128.4° C.

Using essentially the same procedure, but using the appropriately substituted aniline, the following compounds are obtained:

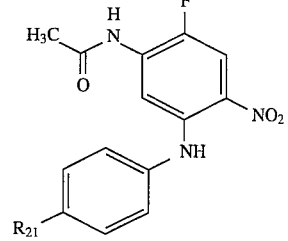

| $R_{21}$ | mp °C. |
|---|---|
| $N(CH_3)_2$ | 224 |
| $OCF_3$ | 174 |
| $CH_3$ | 212–213 |
| $OCH_2C \equiv CH$ | |
| $OCH_2CO_2CH_3$ | |
| $OCH_3$ | |

EXAMPLE 6

Preparation of Methyl 2-[p-(5-acetamido-2-amino-4-fluoroanilino)phenoxy] propionate

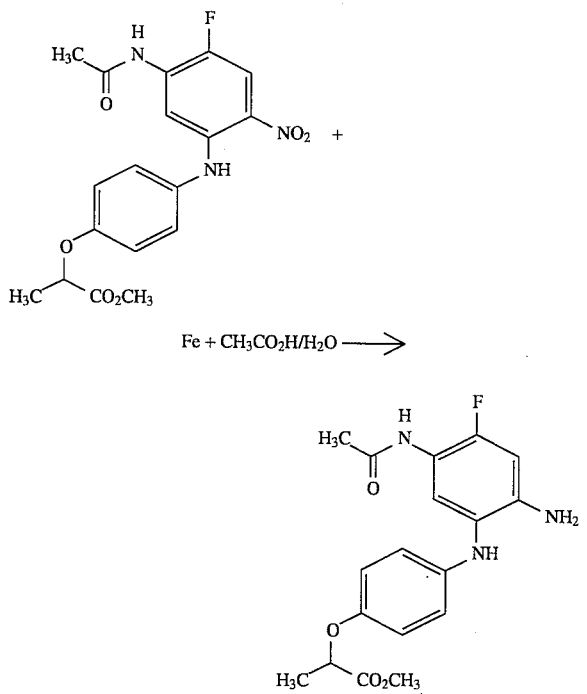

Methyl 2-[p-(5-acetamido-4-fluoro-2-nitroanilino)phenoxy]propionate (8.2 g, 0.021 mol) is added to a mixture of iron dust (3.51 g, 0.063 mol) in a 5% acetic acid solution at 65° C. The reaction mixture is stirred at 65° C. for 2.5 hours, treated with additional iron dust (0.5 g), stirred at 65° C. for 30 minutes, cooled to room temperature and filtered through diatomaceous earth. The resultant filtrate is poured into water and extracted with ethyl acetate. The organic extracts are combined, washed sequentially with saturated sodium hydrogen carbonate solution and water, dried over anhydrous sodium sulfate and concentrated in vacuo to give the title product as a brown-black solid.

Using essentially the same procedure, the following compounds are obtained:

| $R_{21}$ | mp °C. |
|---|---|
| $OCH_3$ | |
| $OCF_3$ | 146–150 |
| $N(CH_3)_2$ | |
| $CH_3$ | |

EXAMPLE 7

Preparation of Methyl 2-[p-(6-acetamido-5-fluoro-1 H-benzotriazol-1-yl)phenoxy] propionate

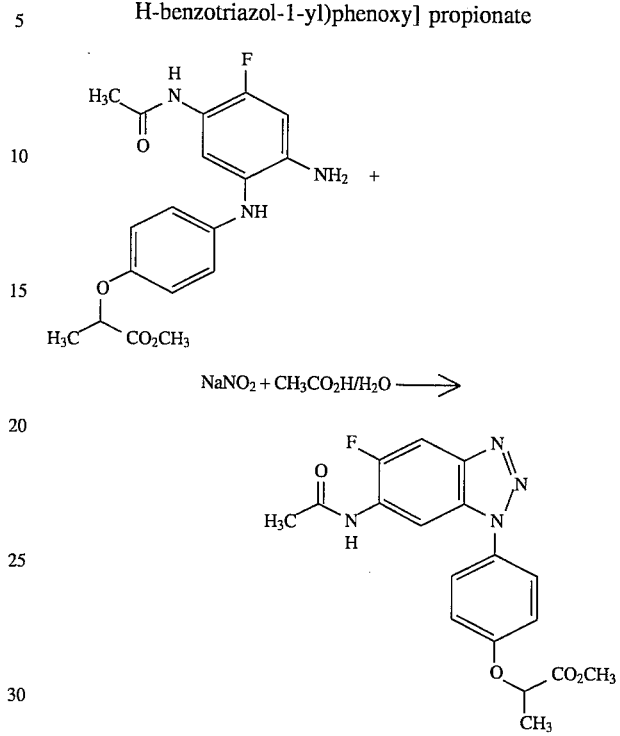

A solution of methyl 2-[p-(5-acetamido-2-amino-4-fluoroanilino)phenoxy]propionate (7 g, 0.019 mol) in tetrahydrofuran is added dropwise to a 50% acetic acid solution at 0° C. To the resultant mixture, a solution of sodium nitrite (2.81 g, 0.041 mol) in water is added dropwise. After the addition is complete, the reaction mixture is warmed to room temperature, stirred for 3 days and poured into water. The aqueous mixture is extracted with ethyl acetate. The organic extracts are combined, washed sequentially with brine and water, dried over anhydrous sodium sulfate and concentrated in vacuo to give the title product as an orange solid which is identified by NMR spectral analyses.

Using essentially the same procedure, the following compounds are obtained:

| $R_{21}$ | mp °C. |
|---|---|
| $OCH_3$ | 204–205 |
| $OCF_3$ | 204–206 |
| $OCHCO_2H$ | |
| $\quad\|$ | |
| $CH_3$ | |
| $N(CH_3)_2$ | 158–160 |

55
-continued

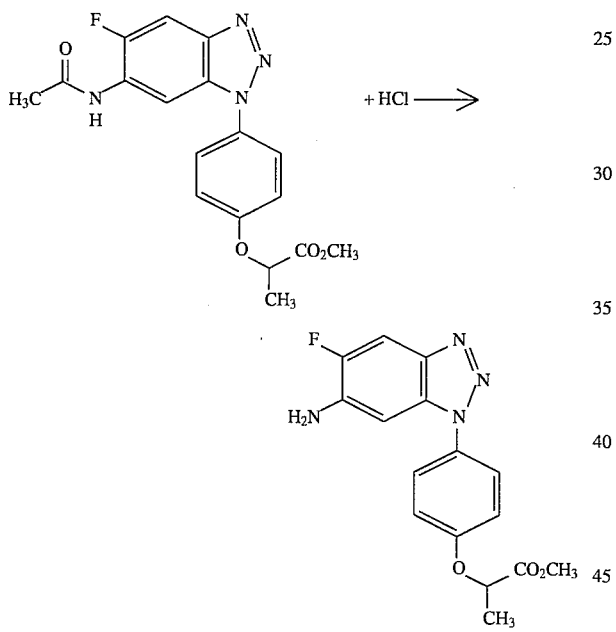

| $R_{21}$ | mp °C. |
|---|---|
| $CH_3$ | 150 (dec.) |

EXAMPLE 8

Preparation of Methyl 2-[p-(6-amino-5-fluoro-1 H-benzotriazol-1-yl)phenoxy] propionate Concentrated hydrochloric acid (6.3 mL) is added to a solution of methyl 2-[p-(6-acetamido-5-fluoro-1 H-benzotriazol-1-yl)phenoxy]propionate (4.77 g, 0.013 mol) in methanol. The reaction mixture is refluxed for 18 hours, cooled to room temperature and concentrated in vacuo to obtain a solid. $^1$HNMR spectral analysis of the solid indicates that ester hydrolysis has occurred. A solution of the solid, sulfuric acid (4 drops) and methanol is refluxed for 6 hours, cooled to room temperature and poured into water. The aqueous mixture is extracted with ethyl acetate. The organic extracts are combined, washed with brine, dried over anhydrous sodium sulfate and concentrated in vacuo to give the title product as a brown powder which is identified by NMR spectral analyses.

Using essentially the same procedure, the following compounds are obtained:

56

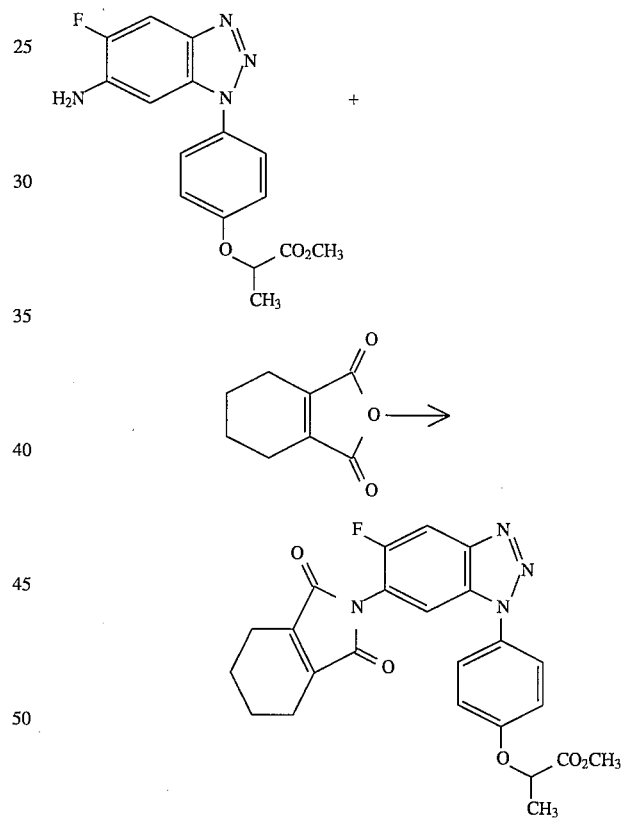

| $R_{21}$ | mp °C. |
|---|---|
| $OCH_3$ | 193–194 |
| $OCF_3$ | 167–170 |
| $N(CH_3)_2$ | |
| $CH_3$ | |

EXAMPLE 9

Preparation of Methyl 2-{p-[6-(1-cyclohexene-1,2 -dicarboximido)-5-fluoro-1H-benzotriazol-1-yl]phenoxy}propionate A solution of methyl 2-[p-(6-amino-5-fluoro-1 H-benzotriazol-1-yl)phenoxy]propionate (3 g, 0.009 mol) and 3,4,5, 6-tetrahydrophthalic anhydride (1.66 g, 0.011 mol) in acetic acid is refluxed for 24 hours, cooled to room temperature and poured into water. The resultant aqueous mixture is extracted with ethyl acetate. The organic extracts are combined, washed sequentially with saturated sodium hydrogen carbonate solution and brine, dried over anhydrous sodium sulfate and concentrated in vacuo to give a residue. Column chromatography of the residue using silica gel and a 10% diethyl ether in methylene chloride solution gives the title product as a beige solid, mp 90°–92° C.

Using essentially the same procedure, the following compounds are obtained:

| | | | |
|---|---|---|---|
| $R_{16}$ | $R_{17}$ | $R_{21}$ | mp °C. |
| —(CH$_2$)$_4$— | | OCH$_3$ | 218–220 |
| —(CH$_2$)$_4$— | | OCF$_3$ | 100–102 |
| —(CH$_2$)$_4$— | | CH$_3$ | 182 |
| —(CH$_2$)$_4$— | | OCH$_2$CO$_2$CH$_3$ | 73–75 |
| —(CH$_2$)$_4$— | | OCH$_2$C≡CH | 144–145 |
| —(CH$_2$)$_4$— | | OH | |
| —CH=CH—CH=CH— | | OCHCO$_2$CH$_3$<br>\|<br>CH$_3$ | 138–142 |
| —CH=CH—N=CH— | | OCHCO$_2$CH$_3$<br>\|<br>CH$_3$ | 193–196 |

EXAMPLE 10

Preparation of
2'-Fluoro-5'-(o-methoxy-anilino)-4'-nitroacetanilide

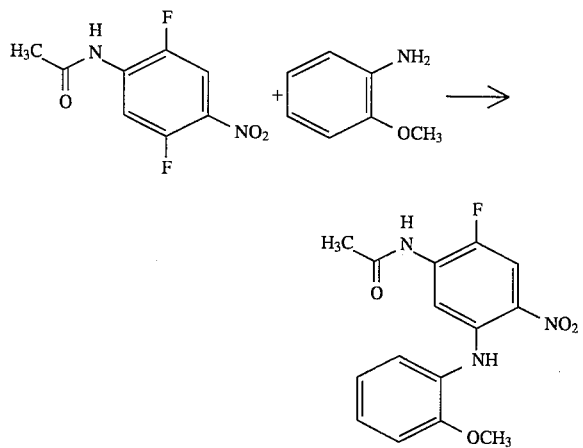

A solution of 2',5'-difluoro-4'-nitroacetanilide (20.0 g, 0.093 mol) and o-anisidine (17.1 g, 0.139 mol) in dioxane is refluxed overnight, treated with additional o-anisidine (5.7 g), refluxed for 5 hours, treated with additional o-anisidine (5.7 g), refluxed for 5 days, treated with N,N-dimethylformamide (50 mL), refluxed overnight, cooled to room temperature and poured into water. The resultant aqueous mixture is extracted with ethyl acetate. The organic extracts are combined, washed sequentially with water and brine, dried over anhydrous magnesium sulfate and concentrated in vacuo to obtain a red oil. Flash column chromatography of the oil using silica gel and a 5% ethyl acetate in methylene chloride solution gives the title product as a brown solid which is identified by NMR spectral analyses.

EXAMPLE 11

Preparation of
4'-Amino-2'-fluoro-5'-(o-methoxy-anilino)acetanilide

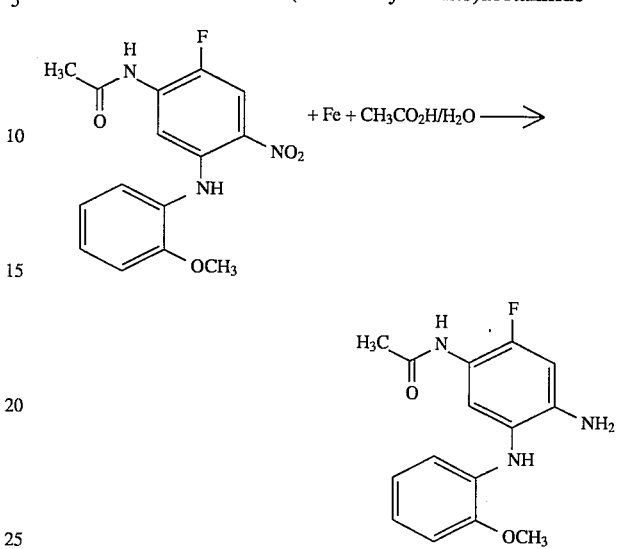

A mixture of 2'-fluoro-5'-(o-methoxyanilino)-4'-nitroacetanilide (14.6 g, 0.046 mol) in ethyl acetate is slowly added to a mixture of iron powder (7.65 g, 0.137 mol) in a 5% acetic acid solution at 65° C. After the addition is complete, the reaction mixture is heated at 65° C. overnight, treated with additional iron powder (2.55 g), heated at 65° C. for one hour and filtered. The resultant filtrate is extracted with ethyl acetate. The organic extracts are combined, washed sequentially with water and brine, dried over anhydrous magnesium sulfate and concentrated in vacuo to obtain a brown oil. Flash column chromatography of the oil using silica gel and 10% to 30% ethyl acetate in methylene chloride solutions gives the title product as a brown oil which is identified by NMR spectral analyses.

EXAMPLE 12

Preparation of N-[5-fluoro-1-(o-methoxphenyl)-1 H-benzotriazol-6-yl]acetamide

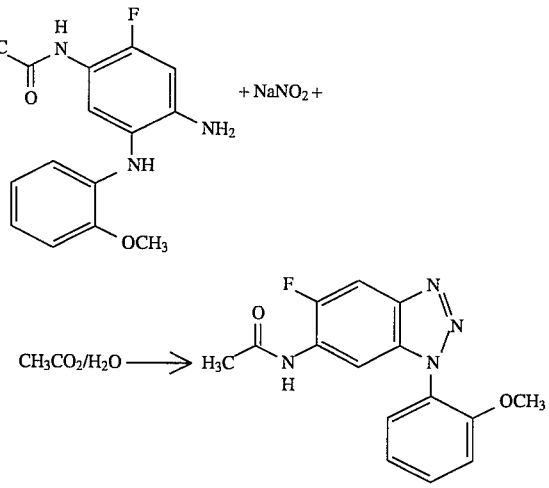

A solution of 4'-amino-2'-fluoro-5'-(o-methoxy-anilino)acetanilide (11.0 g, 0.038 mol) in tetrahydrofuran is added dropwise to a 50% acetic acid solution at 0° C. To the resultant mixture, a solution of sodium nitrite (5.51 g, 0.080 mol) in water is added dropwise. After the addition is complete, the reaction mixture is stirred at room temperature for 2 hours and filtered to obtain a solid. The filtrate is extracted with ethyl acetate and the organic extracts are combined, washed sequentially with water and brine, dried over anhydrous magnesium sulfate and concentrated in vacuo to obtain a dark solid. Flash column chromatography of the combined solids using silica gel and a (3:1) methylene chloride/ethyl acetate solution gives the title product as a greenish-brown solid, mp 174°–175° C.

EXAMPLE 13

Preparation of
6-Amino-5-fluoro-1-(o-methoxyphenyl)-
1H-benzotriazole

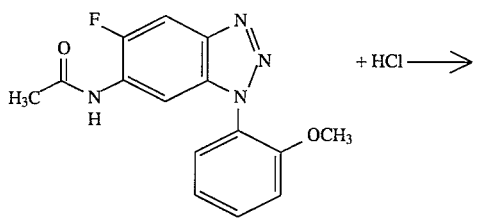

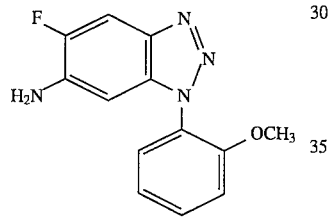

A mixture of N-[5-fluoro-1-(o-methoxyphenyl)-1 H-benzotriazol-6-yl]acetamide (7.14 g, 0.024 g) and concentrated hydrochloric acid (18 mL) in ethanol is refluxed for 2 hours, cooled to room temperature, brought to about pH 5.5 with 3M sodium hydroxide solution and poured into water. The resultant aqueous mixture is extracted with ethyl acetate. The organic extracts are combined, washed sequentially with water and brine, dried over anhydrous magnesium sulfate and concentrated in vacuo to obtain a dark, brown oil. Flash column chromatography of the oil using silica gel and 5% to 10% ethyl acetate in methylene chloride solutions gives the title product as an orange solid, mp 128°–129° C.

EXAMPLE 14

Preparation of N-[5-fluoro-1-(o-methoxyphenyl)-1
H-benzotriazol-6-yl]-1-cyclohexene-1,2-dicarboximide

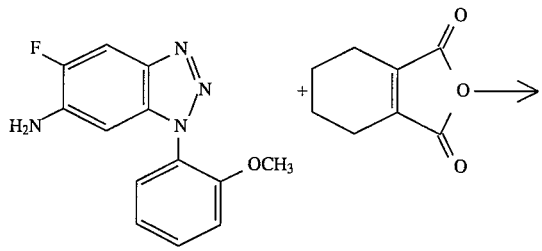

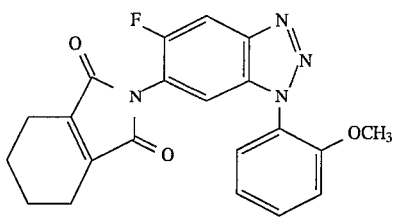

A solution of 6-amino-5-fluoro-1-(o-methoxyphenyl)-1H-benzotriazole (5.10 g, 0.019 mol) and 3,4,5,6-tetrahydrophthalic anhydride (3.68 g, 0.024 mol) in acetic acid is refluxed for 6 hours, cooled to room temperature and poured into water. The resultant aqueous mixture is extracted with ethyl acetate. The organic extracts are combined, washed sequentially with water and brine, dried over anhydrous magnesium sulfate and concentrated in vacuo to obtain an orange oil. Flash column chromatography of the oil using silica gel and 2.5% to 5% ethyl acetate in methylene chloride solutions gives the title product as an orange solid, mp 83°–87° C.

EXAMPLE 15

Preparation of N-[5-fluoro-1-(o-hydroxyphenyl)-1
H-benzotriazole-6-yl]-1-cyclohexene-1,2-dicarboximide

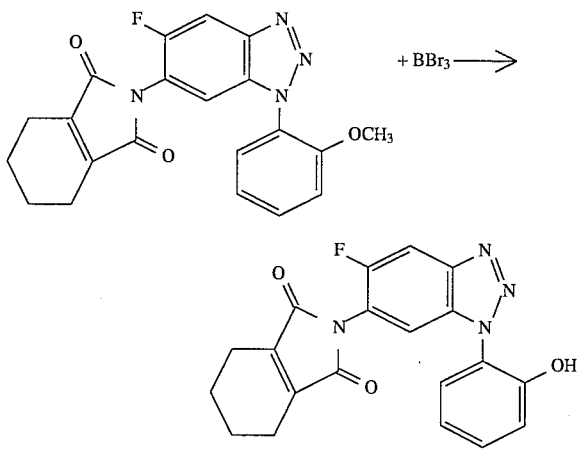

A solution of N-[5-fluoro-1-(o-methoxyphenyl-1 H-benzotriazol-6-yl]-1-cyclohexene-1,2-dicarboximide (1.00 g, 0.003 mol) in methylene chloride is slowly added to a one molar boron tribromide in methylene chloride solution (5 mL, 0.005 mol) at −20° C. The reaction mixture is stirred at room temperature overnight, washed sequentially with water and brine, dried over anhydrous magnesium sulfate and concentrated in vacuo to obtain a tan solid. Flash column chromatography of the solid using silica gel and 2.5% to 10% ethyl acetate in methylene chloride solutions gives the title product as a white solid, mp 274°–275° C.

EXAMPLE 16

Preparation of Methyl {o-[6-(1-cyclohexene-1,2-dicarboximido)-5-fluoro-1H-benzotriazol-1-yl]phenoxy}acetate

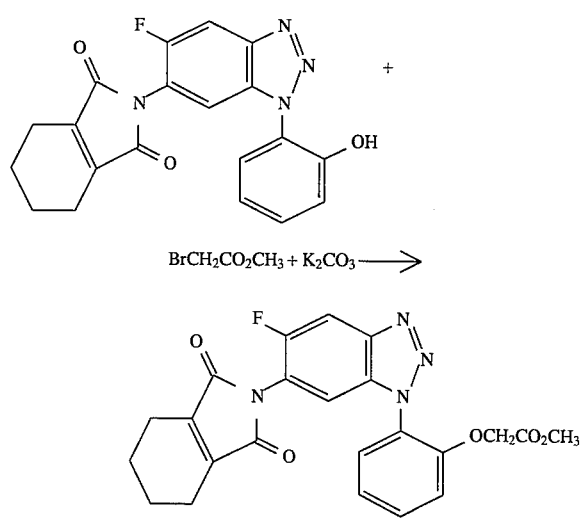

A mixture of N-[5-fluoro-1-(o-hydroxyphenyl)-1 H-benzotriazol-6-yl]-1-cyclohexene-1,2-dicarboximide (0.75 g, 0.002 mol), potassium carbonate (0.41 g, 0.003 mol) and methyl bromoacetate (0.37 g, 0.002 mol) in N,N-dimethylformamide is stirred at room temperature overnight and poured into water. The aqueous mixture is extracted with ethyl acetate. The organic extracts are combined, washed sequentially with water and brine and concentrated in vacuo to obtain a yellow oil. Flash column chromatography of the oil using silica gel and 2.5% to 5% ethyl acetate in methylene chloride solutions gives the title product as a white solid, mp 79°–81° C.

Using essentially the same procedure, the following compounds are obtained:

| $R_{22}$ | mp °C. |
|---|---|
| $CH_2CO_2H$ | 135 (dec.) |
| $CHCO_2CH_3$<br>\|<br>$CH_3$ | 187–189 |

EXAMPLE 17

Preemergence Herbicidal Evaluation of Test Compounds

The preemergence herbicidal activity of the test compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.125 to 0.500 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth below. Data obtained are reported in Table I below. Where more than one test is involved for a given compound, the data are averaged.

Plant species employed in these evaluations are reported by header abbreviation, common name and scientific name.

Compounds employed in this preemergence herbicidal evaluation and in the postemergence evaluation in the following example are given a compound number and identified by name. Data in Table I are reported by compound number.

Herbicide Rating Scale

Results of herbicide evaluation are expressed on a rating scale (0–9). The scale is based upon a visual observation of plant stand, vigor, malformation, size, chlorosis and overall plant appearance as compared with a control.

| Rating | Meaning | Control Compared to Check |
|---|---|---|
| 9 | Complete kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |
| — | No Evaluation | |

| PLANT SPECIES EMPLOYED IN HERBICIDAL EVALUATIONS | | |
|---|---|---|
| Header Abb. | Common Name | Scientific Name |
| ABUTH | VELVETLEAF | ABUTILON THEOPHRASTI, MEDIC. |
| AMARE | PIGWEED, REDROOT | AMARANTHUS RETRO- |

-continued

PLANT SPECIES EMPLOYED IN HERBICIDAL EVALUATIONS

| Header Abb. | Common Name | Scientific Name |
| --- | --- | --- |
| AMBEL | RAGWEED, COMMON | FLEXUS, L. AMBROSIA ARTEMISII-FOLIA, L. |
| CASOB | SICKLEPOD | CASSIA OBTUSIFOLIA, L. |
| CHEAL | LAMBSQUARTERS, COMMON | CHENOPODIUM ALBUM, L. |
| IPOHE | MORNINGGLORY, IVYLEAF | IPOMOEA HEDERACEA, (L) JACQ. |
| IPOSS | MORNINGGLORY SPP. | IPOMOEA SPP. |
| DIGSA | CRABGRASS, (HAIRY) L | DIGITARIA SANGUINALIS, (L) SCOP |
| ECHCG | BARNYARDGRASS | ECHINOCHLOA CRUS-GALLI, (L) BEAU |
| GLXMAW | SOYBEAN, WILLIAMS | GLYCINE MAX(L)MERR. CV. WILLIAMS |
| ORYSAT | RICE, TEBONNET | ORYZA SATIVA, L. TEBONNET |
| ORYSA | RICE (UNSPECIFIED) | ORYZA SATIVA L. (UNSPECIFIED) |
| ZEAMX | CORN, FIELD | ZEA MAYS L. (SAMMEL-BEZEICHNUNG) |

COMPOUNDS EVALUATED AS HERBICIDAL AGENTS

| Compound Number | |
| --- | --- |
| 1 | Methyl 2-{p-[6-(1-cyclohexene-1,2-dicarboximido)-5-fluoro-1H-benzotriazol-1-yl]phenoxy}propionate |
| 2 | N-[5-fluoro-1-(p-methoxyphenyl)-1H-benzotriazol-6-yl]-1-cyclohexene-1,2-dicarboximide |
| 3 | N-{5-fluoro-1-[p-(trifluoromethoxy)phenyl]-1H-benzotriazol-6-yl}-1-cyclohexene-1,2-dicarboximide |
| 4 | N-[5-fluoro-1-(p-tolyl)-1H-benzotriazol-6-yl]-1-cyclohexene-1,2,-dicarboximide |
| 5 | Methyl 2-[p-(5-fluoro-6-maleimido-1H-benzotriazol-1-yl)phenoxy]propionate |
| 6 | Methyl 2-{p-[5-fluoro-6-(3,4-pyridinedicarboximido)-1H-benzotriazol-1-yl]phenoxy}-propionate |
| 7 | Methyl 2-[p-(5-fluoro-6-phthalimido-1H-benzotriazol-1-yl)phenoxy]propionate |
| 8 | Methyl {p-[6-(1-cyclohexene-1,2-dicarboximido)-5-fluoro-1H-benzotriazol-1-yl]phenoxy}acetate |
| 9 | N-{5-fluoro-1-[p-(2-propynyloxy)phenyl]-1H-benzotriazol-6-yl}-1-cyclohexene-1,2-dicarboximide |
| 10 | N-[5-fluoro-1-(o-methoxyphenyl)-1H-benzotriazol-6-yl]-1-cyclohexene-1,2-dicarboximide |
| 11 | N-[5-fluoro-1-(o-hydroxyphenyl)-1H-benzotriazol-6-yl]-1-cyclohexene-1,2-dicarboximide |
| 12 | Methyl {o-[6-(1-cyclohexene-1,2-dicarboximido)-5-fluoro-1H-benzotriazol-1-yl]phenoxy}acetate |
| 13 | Methyl 2-{o-[6-(1-cyclohexene-1,2-dicarboximido)-5-fluoro-1H-benzotriazol-1-yl]phenoxy}propionate |
| 14 | {o-[6-(1-Cyclohexene-1,2-dicarboximido)-5-fluoro-1H-benzotriazol-1-yl]phenoxy}acetic acid |

TABLE I

Preemergence Herbicidal Evaluations of Test Compounds

| Compound Number | Rate (kg/ha) | ABUTH | AMARE | AMBEL | CASOB | CHEAL | IPOHE | IPOSS | DIGSA | ECHCG | GLXMAW | ORYSAT | ORYSA | ZEAMX |
|---|---|---|---|---|---|---|---|---|---|---|---|---|---|---|
| 1 | 0.500 | 5.0 | — | 8.0 | 4.0 | 9.0 | — | 8.0 | — | — | 4.0 | — | — | 6.0 |
|   | 0.250 | 6.0 | — | 8.0 | 0.0 | 9.0 | — | 4.0 | — | — | 2.0 | — | — | 3.0 |
|   | 0.125 | 2.5 | 8.0 | 7.0 | 0.0 | 9.0 | 9.0 | 2.0 | 0.0 | 0.0 | 1.0 | — | 0.0 | 1.0 |
| 2 | 0.500 | 9.0 | — | 5.0 | 4.0 | 9.0 | — | 8.0 | — | — | 2.0 | — | — | 0.0 |
|   | 0.250 | 7.0 | — | 4.0 | 5.0 | 9.0 | — | 3.0 | — | — | 0.0 | — | — | 0.0 |
|   | 0.125 | 5.0 | 0.0 | 0.0 | 0.0 | 9.0 | — | 0.0 | 0.0 | 0.0 | 0.0 | 0.0 | — | 1.0 |
| 3 | 0.500 | 9.0 | — | 6.0 | 5.0 | 9.0 | — | 3.0 | — | 0.0 | 0.0 | — | — | 3.0 |
|   | 0.250 | 7.0 | — | 2.0 | 5.0 | 9.0 | — | 5.0 | — | — | 0.0 | — | — | 0.0 |
|   | 0.125 | 5.0 | 8.0 | 2.0 | 2.0 | 9.0 | — | 1.0 | 0.0 | 0.0 | 0.0 | 0.0 | — | 0.0 |
| 4 | 0.500 | 9.0 | 9.0 | 8.5 | 0.0 | 9.0 | — | 8.0 | 9.0 | 2.0 | 1.0 | 0.0 | — | 0.5 |
|   | 0.250 | 9.0 | 9.0 | 8.5 | 5.0 | 9.0 | — | 3.0 | 3.0 | 0.0 | 1.5 | 4.0 | — | 0.5 |
|   | 0.125 | 7.0 | 9.0 | 4.0 | 2.0 | 9.0 | — | 3.0 | 0.0 | 0.0 | 1.0 | 4.0 | — | 0.5 |
| 5 | 0.500 | 0.0 | 0.0 | 0.0 | — | — | 0.0 | — | 0.0 | 0.0 | 0.0 | — | — | 0.0 |
| 6 | 0.500 | 0.0 | 0.0 | 0.0 | — | — | 0.0 | — | 0.0 | 0.0 | 0.0 | — | — | 0.0 |
| 7 | 0.500 | 5.0 | 8.0 | 7.0 | 6.0 | 9.0 | 5.0 | 6.0 | 0.0 | 0.0 | 2.0 | — | 0.0 | 5.5 |
| 8 | 0.500 | 2.0 | 9.0 | 5.0 | 3.0 | 8.0 | 7.0 | 9.0 | 0.0 | 0.0 | 4.5 | — | 2.0 | 1.0 |
|   | 0.250 | 9.0 | — | 4.0 | 0.0 | 6.0 | — | 3.0 | 0.0 | 0.0 | 6.0 | — | — | 0.0 |
|   | 0.125 | 9.0 | 9.0 | 5.0 | — | — | 9.0 | — | 4.0 | 0.0 | 2.0 | — | 2.0 | 0.0 |
| 9 | 0.500 | 9.0 | 9.0 | 9.0 | — | — | 6.0 | — | 9.0 | 8.0 | 0.0 | — | 4.0 | 0.0 |
| 10 | 0.500 | 9.0 | 9.0 | 8.0 | 6.0 | 9.0 | — | 7.5 | 9.0 | 6.0 | 4.0 | — | — | 5.5 |
|    | 0.250 | 9.0 | 0.0 | 0.0 | 5.0 | 9.0 | 0.0 | 6.0 | 0.0 | 6.0 | 6.5 | — | — | 1.0 |
|    | 0.125 | 0.0 | 0.0 | 8.5 | — | — | 5.0 | 9.0 | 4.0 | 0.0 | 2.0 | 0.0 | 0.0 | 0.0 |
| 11 | 0.500 | 9.0 | 0.0 | 0.0 | 9.0 | 9.0 | — | 7.5 | 6.0 | 2.0 | 0.0 | — | 4.0 | 1.0 |
| 12 | 0.500 | 8.0 | 0.0 | 8.5 | 6.0 | 9.0 | — | 7.5 | 5.0 | 4.0 | 5.0 | — | — | 3.5 |
|    | 0.250 | 7.5 | 9.0 | 7.5 | 9.0 | 9.0 | 3.0 | 8.0 | 9.0 | 3.0 | 3.0 | — | — | 1.0 |
|    | 0.125 | 9.0 | 9.0 | 6.5 | 8.0 | 9.0 | — | 9.0 | — | 0.0 | 1.0 | — | 0.0 | 0.5 |
| 13 | 0.500 | 9.0 | 9.0 | 7.5 | 6.0 | 9.0 | — | 7.0 | — | — | 0.0 | — | — | 1.0 |
|    | 0.250 | 9.0 | — | 7.0 | 9.0 | 9.0 | 0.0 | 9.0 | 0.0 | 1.5 | 1.0 | — | 0.0 | 0.0 |
|    | 0.125 | 9.0 | — | 5.0 | 6.0 | 9.0 | — | 4.0 | — | — | 0.0 | — | — | 1.0 |
| 14 | 0.500 | 4.3 | 9.0 | 5.7 | 9.0 | 9.0 | — | 5.0 | — | — | 1.0 | — | 2.0 | 0.0 |
|    | 0.250 | 7.0 | — | 9.0 | 6.0 | 9.0 | — | 4.0 | — | — | 0.0 | — | — | 0.0 |
|    | 0.125 | 4.0 | — | 9.0 | 5.0 | 6.0 | — | — | — | — | 3.0 | — | — | 0.0 |

EXAMPLE 18

Postemergence Herbicidal Evaluation of Test Compounds

The postemergence herbicidal activity of the compounds of the present invention is demonstrated by the following tests, wherein a variety of dicotyledonous and monocotyledonous plants are treated with test compounds, dispersed in aqueous acetone mixtures. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantities to provide the equivalent of about 0.125 kg to 0.500 kg per hectare of test compound when applied to the plants through a spray nozzle operating at 40 psi for a predetermined time. After spraying, the plants are placed on greenhouse benches and are cared for in the usual manner, commensurate with conventional greenhouse practices. From four to five weeks after treatment, the seedling plants are examined and rated according to the rating system provided in Example 17.

The data obtained are reported in Table II below. The compounds evaluated are reported by compound number given in Example 17.

TABLE II

Postemergence Herbicidal Evaluations of Test Compounds

| Compound Number | Rate (kg/ha) | ABUTH | AMARE | AMBEL | CASOB | CHEAL | IPOHE | IPOSS | DIGSA | ECHCG | GLXMAW | ORYSAT | ORYSA | ZEAMX |
|---|---|---|---|---|---|---|---|---|---|---|---|---|---|---|
| 1 | 0.500 | 9.0 | — | 9.0 | — | — | — | 9.0 | 7.0 | 9.0 | — | — | — | 9.0 |
|   | 0.250 | 9.0 | — | 9.0 | — | — | — | 9.0 | 5.0 | 8.0 | — | — | — | 8.0 |
|   | 0.125 | 9.0 | — | 7.0 | 7.0 | 9.0 | — | 9.0 | 5.0 | 6.0 | 7.0 | 2.0 | — | 7.5 |
| 2 | 0.500 | 9.0 | 9.0 | 7.5 | 7.0 | 9.0 | — | 8.0 | 3.0 | 4.0 | 4.5 | 2.0 | — | 3.5 |
|   | 0.250 | 9.0 | 9.0 | 6.0 | 7.0 | 9.0 | — | 6.5 | 2.0 | 3.0 | 5.0 | 3.0 | — | 3.0 |
|   | 0.125 | 9.0 | 9.0 | 5.0 | 5.0 | 9.0 | — | 8.5 | 2.0 | 2.0 | 4.5 | 4.0 | — | 3.0 |
| 3 | 0.500 | — | 9.0 | 9.0 | — | — | — | 9.0 | 3.0 | 5.0 | 4.0 | 3.0 | — | 2.5 |
|   | 0.250 | 9.0 | 9.0 | 7.0 | 7.0 | 9.0 | — | 8.0 | 2.0 | 2.0 | 2.5 | 4.0 | — | 4.0 |
|   | 0.125 | 9.0 | 9.0 | 6.0 | 7.0 | 9.0 | — | 6.5 | 2.0 | 2.0 | 2.0 | 3.0 | — | 2.5 |
| 4 | 0.500 | 9.0 | 9.0 | 9.0 | — | — | — | 8.0 | 4.0 | 3.0 | 5.0 | 2.0 | — | 2.0 |
|   | 0.250 | 9.0 | 9.0 | 8.0 | 7.0 | 9.0 | — | 9.0 | 3.0 | 2.0 | 4.0 | 3.0 | — | 3.0 |
|   | 0.125 | 9.0 | 9.0 | 8.0 | — | — | 0.0 | 8.5 | 2.0 | 2.0 | 5.0 | 3.0 | — | 3.0 |
| 5 | 0.500 | 0.0 | 0.0 | 0.0 | — | — | 0.0 | — | 0.0 | 0.0 | 0.0 | — | 0.0 | 2.5 |
| 6 | 0.500 | 3.0 | 8.0 | 3.0 | — | — | 3.0 | — | 2.0 | 2.0 | 4.0 | — | 2.0 | 0.0 |
|   | 0.250 | 3.0 | 8.0 | 3.0 | — | — | 4.0 | — | 2.0 | 2.0 | 3.0 | — | 1.0 | 3.0 |
|   | 0.125 | 2.0 | 7.0 | 2.0 | — | — | 2.0 | — | 1.0 | 1.0 | 3.0 | — | 1.0 | 3.0 |
| 7 | 0.500 | 5.0 | 9.0 | 3.0 | — | — | 8.0 | — | 3.0 | 4.0 | 4.0 | — | 2.0 | 3.0 |
|   | 0.250 | 5.0 | 9.0 | 3.0 | — | — | 8.0 | — | 4.0 | 5.0 | 3.0 | — | 3.0 | 3.0 |
|   | 0.125 | 5.0 | 9.0 | 5.0 | — | — | 6.0 | — | 4.0 | 4.0 | 3.0 | — | 3.0 | 4.0 |
| 8 | 0.500 | 9.0 | 9.0 | 9.0 | — | — | 9.0 | — | 4.0 | 9.0 | 6.0 | — | 6.0 | 8.0 |
|   | 0.250 | 7.0 | 9.0 | 9.0 | — | — | 9.0 | — | 8.0 | 6.0 | 6.0 | — | 1.0 | 8.0 |
|   | 0.125 | 5.0 | 9.0 | 9.0 | — | — | 9.0 | — | 6.0 | 4.0 | 5.0 | — | 4.0 | 4.0 |
| 9 | 0.500 | 9.0 | 9.0 | 8.0 | — | — | 9.0 | — | 4.0 | 2.0 | 6.0 | — | 4.0 | 3.0 |
|   | 0.250 | 7.0 | 9.0 | 8.0 | — | — | 9.0 | — | 4.0 | 2.0 | 6.0 | — | 4.0 | 3.0 |
|   | 0.125 | 8.0 | 9.0 | 5.0 | — | — | 9.0 | — | 2.0 | 4.0 | 4.0 | — | 3.0 | 3.0 |
| 10 | 0.500 | 9.0 | 9.0 | 9.0 | — | — | 9.0 | — | 9.0 | 8.0 | 4.0 | — | 5.0 | 8.0 |
|    | 0.250 | 9.0 | 9.0 | 9.0 | — | — | 9.0 | — | 8.0 | 8.0 | 7.0 | — | 5.0 | 4.0 |
|    | 0.125 | 9.0 | 9.0 | 9.0 | — | — | 9.0 | — | 8.0 | 7.0 | 6.0 | — | 4.0 | 4.0 |
| 11 | 0.500 | 8.0 | 9.0 | 5.0 | — | — | 5.0 | — | 4.0 | 5.0 | 6.0 | — | 2.0 | 3.0 |
|    | 0.250 | 8.0 | 9.0 | 5.0 | — | — | 5.0 | — | 2.0 | 4.0 | 4.0 | — | 1.0 | 3.0 |
|    | 0.125 | 8.0 | 9.0 | 5.0 | — | — | 5.0 | — | 2.0 | 4.0 | 3.0 | — | 1.0 | 2.0 |
| 12 | 0.500 | 9.0 | 9.0 | 9.0 | — | — | 9.0 | — | 9.0 | 9.0 | 8.0 | — | 8.0 | 9.0 |
|    | 0.250 | 9.0 | 9.0 | 9.0 | — | — | 9.0 | 9.0 | 9.0 | 4.5 | 8.0 | 0.0 | 7.0 | 8.0 |
|    | 0.125 | 9.0 | 9.0 | 9.0 | — | — | 9.0 | 9.0 | 9.0 | 4.5 | 8.0 | 0.0 | 5.0 | 7.0 |
| 13 | 0.500 | 9.0 | 9.0 | 9.0 | — | — | 9.0 | — | 9.0 | 9.0 | 5.0 | — | 4.0 | 7.0 |
|    | 0.250 | 9.0 | 9.0 | 9.0 | — | — | 8.0 | — | 8.0 | 8.0 | 6.0 | — | 4.0 | 6.0 |
|    | 0.125 | 9.0 | 9.0 | 9.0 | — | — | 9.0 | — | 4.5 | 6.5 | 5.0 | — | 3.0 | 4.0 |
| 14 | 0.500 | 9.0 | 9.0 | 9.0 | 9.0 | 9.0 | 9.0 | 9.0 | 3.0 | 3.0 | 5.7 | — | 3.0 | 4.0 |
|    | 0.250 | 8.3 | 9.0 | 8.3 | 9.0 | 9.0 | 7.5 | 9.0 | 3.0 | 3.0 | 5.7 | — | 3.0 | 3.0 |
|    | 0.125 | 9.0 | 9.0 | 7.3 | 7.0 | 9.0 | 6.0 | 9.0 | 1.5 | 2.0 | 3.7 | — | 2.5 | 2.3 |

What is claimed is:

1. A compound having the structural formula

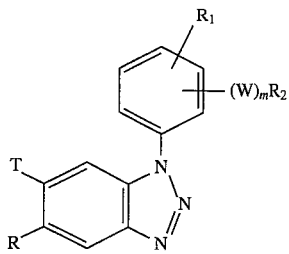

wherein

R is hydrogen, halogen, nitro, cyano, $C_1$–$C_4$alkyl, $C_1$–$C_4$haloalkyl, $C_1$–$C_4$alkoxy, $C_1$–$C_4$haloalkoxy or $R_3S(O)n$;

$R_3$ is $C_1$–$C_4$alkyl optionally substituted with one or more halogen atoms;

n is an integer of 0, 1 or 2;

$R_1$ is hydrogen, halogen, $C_1$–$C_4$alkyl or $C_1$–$C_4$haloalkyl;

$R_2$ is V or $R_4V$;

$R_4$ is $C_1$–$C_5$alkylene optionally substituted with one or more halogen, $C_1$–$C_4$alkyl, $C_1$–$C_4$haloalkyl or $C_3$–$C_6$cycloalkyl groups;

V is hydrogen, halogen, cyano, $C(O)R_5$, $C(Y)R_6$, $CH_2OC(O)R_7$, $CH_2OR_6$, $CH(OR_8)_2$, $N(R_6)SO_2R_9$, $C_2$–$C_6$alkenyl substituted with one $CO_2R_7$ group or $C_2$–$C_6$alkynyl substituted with one $CO_2R_7$ group;

$R_5$ is OH, $OR_{10}$, $NR_{11}R_{12}$ or $N(R_6)SO_2R_9$;

Y is O, $NOC(R_{13}R_{14})CO_2R_8$ or $NOR_7$;

$R_6$ is hydrogen or $C_1$–$C_4$alkyl optionally substituted with $C_1$–$C_4$alkoxy;

$R_7$ is hydrogen, $C_1$–$C_4$alkyl, benzyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups;

$R_8$ is $C_1$–$C_4$alkyl, —$(CH_2)_3$— or —$(CH_2)_4$—;

$R_9$ is $C_1$–$C_4$alkyl, $C_1$–$C_4$haloalkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups;

$R_{10}$ is $C_1$–$C_6$alkyl optionally substituted with $C_1$–$C_4$alkoxy, $C_1$–$C_4$alkylthio, halogen, hydroxy, $C_3$–$C_6$cyclo-alkyl, furyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$-haloalkoxy groups, $C_3$–$C_6$alkenyl optionally substituted with $C_1$–$C_4$alkoxy, halogen, $C_3$–$C_6$cycloalkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$-haloalkoxy groups, $C_3$–$C_6$alkynyl optionally substituted with $C_1$–$C_4$alkoxy or halogen, $C_3$–$C_6$cycloalkyl, $N=C(R_{13}R_{14})$, $C(R_{13}R_{14})CO_2R_6$ or an alkali metal, alkaline earth metal, manganese, copper, zinc, cobalt, silver, nickel, ammonium or organic ammonium cation;

$R_{11}$ and $R_{12}$ are each independently hydrogen, $C_1$–$C_4$alkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups;

$R_{13}$ and $R_{14}$ are each independently hydrogen or $C_1$–$C_4$alkyl;

W is O, S or $NR_{15}$;

$R_{15}$ is hydrogen or $C_1$–$C_4$alkyl;

m is an integer of 0 or 1; and

T is $NH_2$ or

$NHCCH_3$.

2. The compound according to claim 1 wherein

R is hydrogen or halogen;

$R_1$ is hydrogen or $C_1$–$C_4$alkyl;

$R_4$ is methylene optionally substituted with one or two halogen atoms, one $C_1$–$C_4$alkyl group or one $C_1$–$C_4$haloalkyl group;

V is hydrogen, halogen, $C(O)R_5$ or $C_2$–$C_6$alkynyl;

$R_5$ is OH or $OR_{10}$;

$R_{10}$ is $C_1$–$C_6$alkyl;

W is O; and

T is $NH_2$ or

$NHCCH_3$.

* * * * *